United States Patent
Shigeyama et al.

(10) Patent No.: US 11,872,304 B2
(45) Date of Patent: Jan. 16, 2024

(54) TOPICAL COMPOSITION

(71) Applicants: JINNO INSTITUTE, Nagoya (JP); OTSUKA PHARMACEUTICAL FACTORY, INC., Naruto (JP)

(72) Inventors: Masato Shigeyama, Seki (JP); Toshiya Nagiri, Naruto (JP); Yuki Takeuchi, Naruto (JP); Yu Mima, Naruto (JP); Katsunori Shirai, Naruto (JP); Toshimitsu Terao, Naruto (JP)

(73) Assignees: JINNO INSTITUTE, Nagoya (JP); OTSUKA PHARMACEUTICAL FACTORY, INC., Naruto (JP)

( * ) Notice: Subject to any disclaimer, the term of this patent is extended or adjusted under 35 U.S.C. 154(b) by 0 days.

(21) Appl. No.: 17/059,534

(22) PCT Filed: May 29, 2019

(86) PCT No.: PCT/JP2019/021182
§ 371 (c)(1),
(2) Date: Nov. 30, 2020

(87) PCT Pub. No.: WO2019/230750
PCT Pub. Date: Dec. 5, 2019

(65) Prior Publication Data
US 2021/0205210 A1    Jul. 8, 2021

(30) Foreign Application Priority Data

May 29, 2018  (JP) .................................. 2018-102152

(51) Int. Cl.
| | |
|---|---|
| A61K 9/00 | (2006.01) |
| A61K 9/06 | (2006.01) |
| A61K 33/30 | (2006.01) |
| A61K 47/02 | (2006.01) |
| A61K 47/10 | (2017.01) |
| A61K 47/38 | (2006.01) |

(52) U.S. Cl.
CPC ............. *A61K 9/0014* (2013.01); *A61K 9/06* (2013.01); *A61K 33/30* (2013.01); *A61K 47/02* (2013.01); *A61K 47/10* (2013.01); *A61K 47/38* (2013.01)

(58) Field of Classification Search
CPC ........ A61K 9/06; A61K 9/0014; A61K 33/30; A61K 47/32; A61K 47/38; A61K 47/36; A61K 47/10; A61K 47/02; A61K 2300/00; A61P 17/00
See application file for complete search history.

(56) References Cited

U.S. PATENT DOCUMENTS

| | | | | |
|---|---|---|---|---|
| 5,256,396 A | * | 10/1993 | Piechota, Jr. .......... | A61Q 11/00 424/49 |
| 5,624,962 A | * | 4/1997 | Takeuchi ............... | A61K 47/10 424/78.02 |
| 2002/0114778 A1 | * | 8/2002 | Xia ........................ | A61K 47/10 424/78.38 |
| 2002/0150630 A1 | * | 10/2002 | Brooks ................ | A61K 31/337 424/749 |
| 2003/0092754 A1 | | 5/2003 | Nishimuta et al. | |
| 2005/0170013 A1 | | 8/2005 | Douglas | |
| 2006/0057385 A1 | * | 3/2006 | Schumacher .......... | C01G 23/07 428/404 |
| 2013/0251645 A1 | * | 9/2013 | Won ........................ | A61K 8/29 264/165 |
| 2018/0318343 A1 | | 11/2018 | Udagawa et al. | |

FOREIGN PATENT DOCUMENTS

| | | |
|---|---|---|
| JP | 52-102417 A | 8/1977 |
| JP | 2001-288086 A | 10/2001 |
| JP | 2007-520551 A | 7/2007 |
| JP | 2011-121932 A | 6/2011 |
| WO | 2007/148832 A1 | 12/2007 |
| WO | 2016/199907 A1 | 12/2016 |
| WO | 2018/105739 A1 | 6/2018 |

OTHER PUBLICATIONS

"Chemosurgical Treatment", Medicine and Drug Journal, 2005, pp. 2289-2294, vol. 41,No. 9.
Hiromitsu Yamamoto et al., "Formulation Study of Mohs Paste for Chemosurgery", Journal of Pharmaceutical Science and Technology, 2015, pp. 264-270, vol. 75, No. 4.
Maho Taguchi et al., "Preparation and Evaluation of Modified Mohs Paste without Starch", The Pharmaceutical Society of Japan, 2017, pp. 477-484, vol. 137, No. 4.
Sumiko Takatsuka et al., "Minimally Invasive Treatment for Skin Cancer: Topics of Topical Drugs", Journal of Niigata Cancer Center Hospital, Mar. 2013, pp. 6-10, vol. 53, No. 1 pp. 6-10.
International Search Report for PCT/JP2019/021182 dated, Jul. 16, 2019 (PCT/ISA/210).

* cited by examiner

*Primary Examiner* — Doan T Phan
(74) *Attorney, Agent, or Firm* — Sughrue Mion, PLLC

(57) ABSTRACT

The purpose of the present invention is to provide an ointment preparation in which both separation over time and discoloration over time are suppressed. Both separation over time and discoloration over time are suppressed in: a topical composition containing (A) 30-60 weight % of zinc chloride, a specific (B) inorganic powder and a specific (C) additive, and (D) a solvent; and a topical composition containing (A) 30-60 weight % of zinc chloride, a specific (B) inorganic powder, and (D) a solvent.

16 Claims, 1 Drawing Sheet

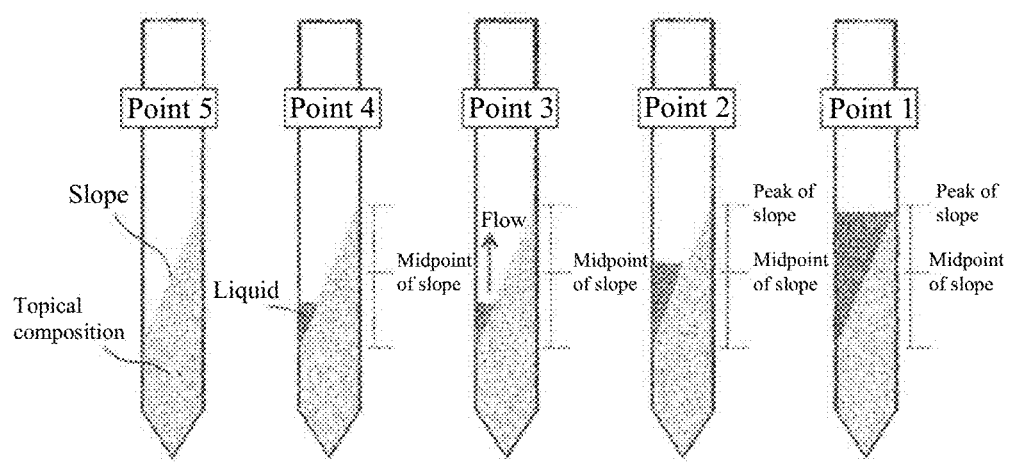

TOPICAL COMPOSITION

CROSS REFERENCE TO RELATED APPLICATIONS

This application is a National Stage of International Application No. PCT/JP2019/021182 filed May 29, 2019, claiming priority based on Japanese Patent Application No. 2018-102152 filed May 29, 2018.

TECHNICAL FIELD

The present invention relates to a topical composition. More specifically, the present invention relates to an ointment with improved suppression of separation and coloration with time.

BACKGROUND ART

Ointments include drugs used for treatment of skin malignancies, skin lesions of breast cancer and the like, and their effectiveness and necessity are widely recognized. For example, an ointment containing zinc chloride as an active ingredient and having an effect of stopping bleeding or exudate at a cancerous skin ulcer site that cannot be controlled by a usual hemostatic agent is known as Mohs' ointment.

This preparation has been improved from the original formulation studied by Frederic Edward Mohs, in terms of raw material availability, applicability to affected areas, and prevention of viscosity increase with time. Known improved formulations include so-called starch formulations (Non-Patent Document 1), sorbitol formulations (Non-Patent Document 2), macrogol formulations (Non-Patent Document 3), and the like. The starch formulation is composed of readily available raw materials such as zinc chloride, zinc oxide, glycerin, water and starch and is actually used as an in-hospital preparation. The sorbitol formulation has improved applicability by further adding sorbitol to the starch formulation. The macrogol formulation is one that replaces the starch and sorbitol of the sorbitol formulation with macrogol and crystalline cellulose, and the increase in viscosity with time is relatively suppressed.

PRIOR ART DOCUMENTS

Non-Patent Documents

Non-Patent Document 1: Medical Journal, Vol. 41, No. 9, 2005, p. 2289-2294
Non-Patent Document 2: Pharmaceutics, 75 (4), 264-270 (2015)
Non-Patent Document 3: The Pharmaceutical Society of Japan, 137 (4) 477-484 (2017)

SUMMARY OF THE INVENTION

Problems to be Solved by the Invention

However, there is room for improvement in feeling of use of the starch formulation described above, and there is still a problem of preparation instability in the macrogol formulation. Specifically, although the macrogol formulation has a relatively suppressed increase in viscosity with time, there is a problem that the preparation separates with time. Due to its component characteristics, Mohs' ointment has strong skin irritation to normal sites, and when the preparation is separated, a liquid with strong skin irritation leaks out. That is, the problem of separation of liquid from the preparation (hereinafter, simply referred to as separation) is extremely large for the Mohs' ointment. Therefore, the Mohs' ointment still has to be prepared before use by in-hospital prescription, which is far from commercialization.

The present inventor has conducted various studies on Mohs' ointment, particularly a formulation that suppresses separation with time, which is a problem of the macrogol formulation. In order to suppress the separation, the inventor has focused on maintenance of a dispersed state of components using a thickener, but faced a problem that most thickeners cannot cause a thickening action at low pH peculiar to the Mohs' ointment. Furthermore, even if a formulation that can suppress separation with time with a thickener is found, this time, the inventor has faced a new problem that coloration (discoloration) occurs with time. That is, it has been found that the macrogol formulation of Mohs' ointment has peculiar problems of separation with time and coloration (discoloration) with time.

Therefore, an object of the present invention is to provide a preparation technology of an ointment in which both separation with time and coloration with time are suppressed.

Means for Solving the Problem

As a result of diligent studies, the present inventor has found that, in a topical composition containing zinc chloride as an active ingredient, which is applied to bleeding or exudate at a cancerous skin ulcer site, excellent preparation stability capable of suppressing both separation with time and coloration with time can be obtained by blending hypromellose, methylcellulose, and/or an esterified product thereof (hereinafter, may be referred to as methylcelluloses); polyvinyl alcohol and/or derivatives thereof; or polyoxyethylene polyoxypropylene glycol, as a specific additive, and/or blending a specific inorganic powder. The present invention has been accomplished by further studies based on this knowledge.

That is, the present invention provides inventions of the following aspects.

Item 1. A topical composition containing (A) 30 to 60% by weight of zinc chloride; (B) inorganic powder and (C) additive; and (D) solvent, in which the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate, and the component (C) is selected from the group consisting of (c1) a cellulous derivative in which a hydroxyl group of cellulose is substituted with a substituent selected from the group consisting of $—OR^1$ group, $—OR^2OH$ group, $—OR^3OR^4$ group, and $—OCOR^5$ group ($R^1$ represents an alkyl group having 1 to 3 carbon atoms, $R^2$ represents an alkylene group having 2 to 3 carbon atoms, $R^3$ represents an alkylene group having 1 to 3 carbon atoms, $R^4$ represents an alkyl group having 1 to 3 carbon atoms, and $R^5$ represents an organic group), (c2) a polyvinyl-type alcohol selected from the group consisting of polyvinyl alcohol and a derivative thereof, and (c3) polyoxyethylene polyoxypropylene glycol.

Item 2. A topical composition containing (A) 30 to 60% by weight of zinc chloride; (B) inorganic powder; and (D) solvent, in which the component (C) is selected from the group consisting of (c1) a cellulous derivative in which a hydroxyl group of cellulose is substituted with a substituent selected from the group consisting of —OR$^1$ group, —OR$^2$OH group, —OR$^3$OR$^4$ group, and —OCOR$^5$ group (R$^1$ represents an alkyl group having 1 to 3 carbon atoms, R$^2$ represents an alkylene group having 2 to 3 carbon atoms, R$^3$ represents an alkylene group having 1 to 3 carbon atoms, R$^4$ represents an alkyl group having 1 to 3 carbon atoms, and R$^5$ represents an organic group), (c2) a polyvinyl-type alcohol selected from the group consisting of polyvinyl alcohol and a derivative thereof, and (c3) polyoxyethylene polyoxypropylene glycol and the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate Item 3. The topical composition according to item 2, further containing (C) additive, in which the component (C) is selected from the group consisting of (c1) a cellulous derivative in which a hydroxyl group of cellulose is substituted with a substituent selected from the group consisting of —OR$^1$ group, —OR$^2$OH group, —OR$^3$OR$^4$ group, and —OCOR$^5$ group (R$^1$ represents an alkyl group having 1 to 3 carbon atoms, R$^2$ represents an alkylene group having 2 to 3 carbon atoms, R$^3$ represents an alkylene group having 1 to 3 carbon atoms, R$^4$ represents an alkyl group having 1 to 3 carbon atoms, and R$^5$ represents an organic group), (c2) a polyvinyl-type alcohol selected from the group consisting of polyvinyl alcohol and a derivative thereof, and (c3) polyoxyethylene polyoxypropylene glycol.

Item 4. The topical composition according to item 1 or 3, in which the component (c1) is selected from the group consisting of methylcellulose, ethylcellulose, hypromellose, hydroxyethylcellulose, hydroxypropylcellulose, methyl hydroxyethyl cellulose, and an esterified product thereof.

Item 5. The topical composition according to any one of items 1 to 4, in which the component (D) is water.

Item 6. The topical composition according to any one of items 1 to 5, further containing (E) polyethylene glycol.

Item 7. The topical composition according to any one of items 1 and 3 to 6, further containing polyoxyethylene polyoxypropylene glycol when the component (C) is the component (c1).

Item 8. The topical composition according to any one of items 1 to 7, in which a sum of products of a viscosity grade of each of the components (c1) and a weight ratio when a total weight of the components (c1) is 1 is 50 mPa·s or more.

Item 9. The topical composition according to item 7, in which a sum of products of a viscosity grade of each of the components (c1) and a weight ratio when a total weight of the components (c1) is 1 is less than 50 mPa·s.

Item 10. The topical composition according to any one of items 1 to 9, further containing (F) polyhydric alcohol.

Item 11. The topical composition according to item 10, in which the component (F) is glycerin.

Item 12. The topical composition according to any one of items 2 to 11, in which the component (B) contains titanium oxide.

Item 13. The topical composition according to any one of items 2 to 11, in which the component (B) is silicon dioxide and titanium oxide.

Item 14. The topical composition according to any one of items 1 to 13, which is a commercially available preparation.

Item 15. A method for suppressing separation and coloration in a topical composition containing (A) 30 to 60% by weight of zinc chloride and (D) solvent, including, in the topical composition, blending (B) inorganic powder and (C) additive together with the component (A) and the (D), in which the component (C) is (c1) a cellulous derivative in which a hydroxyl group of cellulose is substituted with a substituent selected from the group consisting of —OW group, —OR$^2$OH group, —OR$^3$OR$^4$ group, and —OCOR$^5$ group (R$^1$ represents an alkyl group having 1 to 3 carbon atoms, R$^2$ represents an alkylene group having 2 to 3 carbon atoms, R$^3$ represents an alkylene group having 1 to 3 carbon atoms, R$^4$ represents an alkyl group having 1 to 3 carbon atoms, and R$^5$ represents an organic group); (c2) a polyvinyl-type alcohol selected from the group consisting of polyvinyl alcohol and a derivative thereof; or (c3) polyoxyethylene polyoxypropylene glycol, and the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate.

Item 16. A method for suppressing separation and coloration in a topical composition containing (A) 30 to 60% by weight of zinc chloride and (D) solvent, including in the topical composition, blending (B) inorganic powder together with the component (A) and the (D), in which the component (B) is selected from the group consisting of silicon dioxide, aluminum silicate, magnesium silicate, magnesium aluminum silicate, sodium magnesium silicate, calcium silicate, talc, calamine, titanium oxide, iron oxide, aluminum hydroxide, calcium phosphate, and magnesium phosphate.

Advantages of the Invention

According to the present invention, both separation with time and coloration with time can be suppressed, so that ointment can be provided with excellent preparation stability.

BRIEF DESCRIPTION OF THE DRAWINGS

FIG. 1 shows evaluation criteria for the degree of separation suppression of topical compositions adopted in Examples and Comparative Examples.

EMBODIMENTS OF THE INVENTION

1. Topical Composition

The topical composition of the present invention (hereinafter, may be also referred to as "first topical composition") contains (A) 30 to 60% by weight of zinc chloride (hereinafter, may be also referred to as "component (A)"), (B) inorganic powder (hereinafter, may be also referred to as "component (B)") and (C) additive (hereinafter, may be also referred to as "component (C)"), and (D) solvent (hereinafter, may be also referred to as "component (D)"); in which the component (C) is selected from the group consisting of (c1) a cellulous derivative (hereinafter, may be also referred to as "component (c1)"), (c2) a polyvinyl-type alcohol (hereinafter, may be also referred to as "component (c2)"), and (c3) polyoxyethylene polyoxypropylene glycol (hereinafter, may be also referred to as "component (c3)"), and the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate.

In addition, the topical composition of the present invention (hereinafter, may be also referred to as "second topical composition") contains (A) 30 to 60% by weight of zinc chloride (hereinafter, may be also referred to as "component (A)"), (B) inorganic powder (hereinafter, may be also referred to as "component (B)"), and (D) solvent (hereinafter, may be also referred to as "component (D)"); in which the component (B) is selected from the group consisting of silicon dioxide, aluminum silicate, magnesium silicate, magnesium aluminum silicate, sodium magnesium silicate, calcium silicate, talc, calamine, titanium oxide, iron oxide, aluminum hydroxide, calcium phosphate, and magnesium phosphate. Hereinafter, the topical composition of the present invention will be described in detail.

(A) Zinc Chloride

The topical composition of the present invention contains a specific concentration of zinc chloride as the component (A). Zinc chloride is a known component as a component of Mohs' ointment.

Zinc chloride is present in a form of zinc ions in the component (D). The zinc ion has astringent and corrosive actions of a tissue based on a protein denaturing action, and a bactericidal action. Therefore, zinc chloride works well in fixing tumors, stopping bleeding and suppressing exudates associated therewith, reducing foul smell due to secondary infection, and the like. The zinc chloride used in the present invention can be used without particular limitation as long as it can be used as a topical composition. Examples thereof include zinc chloride listed in the 17th revised Japanese Pharmacopoeia.

The content of zinc chloride in the topical composition of the present invention is 30 to 60% by weight. The preferred lower limit of the content of zinc chloride is, for example, 40% by weight or more from the viewpoint of more effectively obtaining an effect of zinc chloride, and 55% by weight or less and more preferably 50% by weight or less from the viewpoint of more preferably obtaining separation suppression and alleviating hardening of tissue and irritation to skin. Specific preferred ranges of the content of zinc chloride are 30 to 55% by weight, 30 to 50% by weight, 40 to 55% by weight, and 40 to 50% by weight.

(B) Inorganic Powder

The topical composition of the present invention contains a predetermined inorganic powder as the component (B). The component (B) acts as a suppressor of separation and coloration in the topical composition containing the components (A) and (D).

The component (B) is selected from the group consisting of at least silicon dioxide, aluminum silicate, magnesium silicate, magnesium aluminum silicate, sodium magnesium silicate, calcium silicate, talc, calamine (formulation of zinc oxide and iron oxide), titanium oxide, iron oxide, aluminum hydroxide, calcium phosphate, and magnesium phosphate. These inorganic powders can be used alone or in combination of two or more types. The silicon dioxide is preferably soft silicic anhydride.

In the first topical composition of the present invention, a component that can be selected as the component (B) includes zinc oxide in addition to the above. That is, when the topical composition of the present invention contains the component (C), the component (B) is selected from the group consisting of silicon dioxide, aluminum silicate, magnesium silicate, magnesium aluminum silicate, sodium magnesium silicate, calcium silicate, talc, calamine (formulation of zinc oxide and iron oxide), zinc oxide, titanium oxide, iron oxide, aluminum hydroxide, calcium phosphate, and magnesium phosphate. These inorganic powders can be used alone or in combination of two or more types.

That is, in the second topical composition of the present invention, zinc oxide is not contained in the component that can be selected as the component (B), and the component (B) is selected from the group consisting of silicon dioxide, aluminum silicate, magnesium silicate, magnesium aluminum silicate, sodium magnesium silicate, calcium silicate, talc, calamine (formulation of zinc oxide and iron oxide), titanium oxide, iron oxide, aluminum hydroxide, calcium phosphate, and magnesium phosphate.

Among these components (B), silicon dioxide, talc, titanium oxide, and zinc oxide are preferable from the viewpoint of even more preferably obtaining separation suppression and coloration suppression.

Moreover, further preferable component (B) includes silicon dioxide, titanium oxide, and zinc oxide, from the viewpoint of suppressing the viscosity of the topical composition from being excessive and/or the viewpoint of facilitating uniform mixing during preparation of the topical composition to obtain good appearance. By suppressing the viscosity of the topical composition from being excessive, it becomes easy to take it out from a container (particularly, a tube). This effect is particularly effective when the topical composition of the present invention is prepared as a commercially available preparation.

Further, further preferable component (B) includes silicon dioxide and zinc oxide, from the viewpoint of suppressing fluidity of the topical composition. Among these, silicon dioxide is preferable in that the fluidity of the topical composition can be suppressed without using the component (C). That is, the second topical composition which does not contain zinc oxide as an essential component of the component (B) is excellent in that the fluidity of the topical composition can be suppressed without using the component (C). Suppressing fluidity of the topical composition is particularly effective in preventing the highly irritating topical composition of the present invention, after being applied to a target place, from accidentally flowing to other places.

Furthermore, further preferable component (B) is titanium oxide, from the viewpoint of improving opacity of the topical composition to facilitate confirmation of the applied portion. Improving opacity of the topical composition to facilitate confirmation of the applied portion is particularly effective in applying the highly irritating topical composition of the present invention only to the target place not to accidentally apply to other places.

In the topical composition of the present invention, it is particularly preferable to contain both silicon dioxide and titanium oxide as the component (B), from the viewpoint of efficiently obtaining both suppression of the fluidity and improvement of the opacity of the topical composition.

Moreover, zinc oxide is preferable in that it has astringent, anti-inflammatory and antiseptic actions, as well as an action of suppressing plasma exudation and leukocyte migration due to reduction of capillary permeability to suppress inflammation. The zinc oxide can be used without particular limitation as long as it can be used as a topical composition. Examples thereof include zinc oxide listed in the 17th revised Japanese Pharmacopoeia. In addition, examples of the zinc oxide also include zinc oxide contained as a component of zinc oxide preparations such as zinc oxide starch, zinc white ointment, and phenol and zinc oxide liniment. Examples of the zinc oxide starch, zinc oxide ointment, and phenol and zinc oxide liniment also include those listed in the 17th revised Japanese Pharmacopoeia. When these zinc oxide preparations are used, the amount of zinc oxide contained in the zinc oxide preparation is used so as to be a desired content in the topical composition of the present invention. Also, zinc oxide starch contains 50 g of zinc oxide in 100 g thereof, zinc oxide ointment contains 20 g of zinc oxide in 100 g thereof, and zinc oxide liniment contains 10 g of zinc oxide in 100 g thereof.

The content (total amount) of the component (B) in the topical composition of the present invention is not particularly limited, and can be appropriately determined according to separation suppression and coloration suppression to be exerted. For example, the lower limit of the content of the component (B) is, for example, 4% by weight or more, preferably 5% by weight or more, further preferably 6% by weight or more, and particularly preferably 10% by weight or more, from the viewpoint of more preferably obtaining separation suppression and coloration suppression. Moreover, the upper limit of the content of the component (B) is, for example, 40% by weight or less, preferably 20% by weight or less, more preferably 15% by weight or less, and further preferably 13% by weight or less, from the viewpoint of smoothing properties of the topical composition without solidifying. Specific ranges of the content of the component (B) are 4 to 40% by weight, 4 to 20% by weight, 4 to 15% by weight, 4 to 13% by weight, 5 to 40% by weight, 5 to 20% by weight, 5 to 15% by weight, 5 to 13% by weight, 6 to 40% by weight, 6 to 20% by weight, 6 to 15% by weight, 6 to 13% by weight, 10 to 40% by weight, 10 to 20% by weight, 10 to 15% by weight, and 10 to 13% by weight.

A ratio of the component (A) to the component (B) is not particularly limited, and is determined by the contents of the component (A) and the component (B). The lower limit of the ratio of the component (B) per 100 parts by weight of the component (A) is, for example, 9 parts by weight or more, and preferably 12 parts by weight or more, from the viewpoint of more preferably obtaining separation suppression and coloration suppression. Also, the upper limit of the ratio of the component (B) per 100 parts by weight of the component (A) is, for example, 60 parts by weight or less, preferably 45 parts by weight or less, and more preferably 30 parts by weight or less, from the viewpoint of smoothing properties of the topical composition without solidifying. Specific ranges of the ratio of the component (B) per 100 parts by weight of the component (A) are 9 to 60 parts by weight, 9 to 45 parts by weight, 9 to 30 parts by weight or less, 12 to 60 parts by weight, 12 to 45 parts by weight, and 12 to 30 parts by weight or less.

Among them, when silicon dioxide is blended with the component (B), the lower limit of the content of silicon dioxide is, for example, 3% by weight or more, from the viewpoint of even more favorably suppressing the fluidity, preferably 4% by weight or more, from the viewpoint of improving feeling of use by suppressing spinnability and/or improving spreadability, more preferably 4.5% by weight or more, further preferably 5% by weight or more, and even more preferably 6% by weight or more, from the viewpoint of further facilitating uniform mixing during preparation to obtain easier appearance. In addition, when silicon dioxide is used as the component (B), it is preferable to combine titanium oxide from the viewpoint of further facilitating uniform mixing during preparation to obtain easier appearance. The upper limit of the content of silicon dioxide is, for example, 10% by weight or less, preferably 8% by weight or less, and more preferably 7% by weight or less, from the viewpoint of smoothing properties of the topical composition without solidifying. Specific ranges of the content of silicon dioxide are 3 to 10% by weight, 3 to 8% by weight, 3 to 7% by weight, 4 to 10% by weight, 4 to 8% by weight, 4 to 7% by weight, 4.5. to 10% by weight, 4.5 to 8% by weight, 4.5 to 7% by weight, 5 to 10% by weight, 5 to 8% by weight, 5 to 7% by weight, 6 to 10% by weight, 6 to 8% by weight, and 6 to 7% by weight.

Moreover, when silicon dioxide is blended with the component (B), the lower limit of the ratio of silicon dioxide per 100 parts by weight of the component (A) is, for example, 6.5 parts by weight or more, from the viewpoint of even more favorably suppressing the fluidity, preferably 9 parts by weight or more, from the viewpoint of improving feeling of use by suppressing spinnability and/or improving spreadability, more preferably 10 parts by weight or more, further preferably 11 parts by weight or more, and even more preferably 13.5 parts by weight or more, from the viewpoint of further facilitating uniform mixing during preparation to obtain easier appearance. Further, the upper limit of the ratio of silicon dioxide per 100 parts by weight of the component (A) is, for example, 30 parts by weight or less, preferably 16 parts by weight or less, and more preferably 14 parts by weight or less, from the viewpoint of smoothing properties of the topical composition without solidifying. Specific ranges of the ratio of silicon dioxide per 100 parts by weight of the component (A) are 6.5 to 30 parts by weight, 6.5 to 16 parts by weight, 6.5 to 14 parts by weight or less, 9 to 30 parts by weight, 9 to 16 parts by weight, 9 to 14 parts by weight or less, 10 to 30 parts by weight, 10 to 16 parts by weight, 10 to 14 parts by weight or less, 11 to 30 parts by weight, 11 to 16 parts by weight, 11 to 14 parts by weight or less, 13.5 to 30 parts by weight, 13.5 to 16 parts by weight, and 13.5 to 14 parts by weight or less.

When titanium oxide is blended with the component (B), the lower limit of the content of titanium oxide is, for example, 0.1% by weight or more, preferably 0.5% by weight or more, more preferably 1% by weight or more, and further preferably 3% by weight or more, from the viewpoint of improving opacity. Further, the upper limit of the content of titanium oxide is, for example, 10% by weight or less, preferably 8% by weight or less, and more preferably 7% by weight or less, from the viewpoint of suppressing fluidity. Specific ranges of the content of titanium oxide are 0.1 to 10% by weight, 0.1 to 8% by weight, 0.1 to 7% by weight, 0.5 to 10% by weight, 0.5 to 8% by weight, 0.5 to 7% by weight, 1 to 10% by weight, 1 to 8% by weight, 1 to 7% by weight, 3 to 10% by weight, 3 to 8% by weight, and 3 to 7% by weight.

Also, when titanium oxide is blended with the component (B), the lower limit of the ratio of titanium oxide per 100 parts by weight of the component (A) is, for example, 2 parts by weight or more, preferably 6.5 parts by weight or more, and more preferably 13 parts by weight or more, from the viewpoint of improving opacity. Further, the upper limit of the ratio of titanium oxide per 100 parts by weight of the component (A) is 20 parts by weight or less, and more preferably 15 parts by weight or less, from the viewpoint of suppressing fluidity. Specific ranges of the ratio of titanium oxide per 100 parts by weight of the component (A) are 2 to 20 parts by weight, 2 to 15 parts by weight, 6.5 to 20 parts by weight, 6.5 to 15 parts by weight, 13 to 20 parts by weight, and 13 to 15 parts by weight.

When silicon dioxide and titanium oxide are blended with the component (B), the lower limit of the ratio of titanium oxide per 1 part by weight of silicon dioxide is 0.2 parts by weight or more, and preferably 0.8 parts by weight or more, from the viewpoint of improving opacity. Further, the upper limit of the ratio of titanium oxide per 1 part by weight of silicon dioxide is, for example, 2.8 parts by weight or less, preferably 2 parts by weight or less, and more preferably 1.5 parts by weight or less, from the viewpoint of suppressing fluidity, and the like. Specific ranges of the ratio of titanium oxide per 1 part by weight of silicon dioxide are 0.2 to 2.8 parts by weight, 0.2 to 2 parts by weight, 0.2 to 1.5 parts by weight, 0.8 to 2.8 parts by weight, 0.8 to 2 parts by weight, and 0.8 to 1.5 parts by weight.

When talc is blended with the component (B), the lower limit of the content of talc is, for example, 3% by weight or more, and preferably 5% by weight or more, from the viewpoint of preferably obtaining separation suppression and coloration suppression. The lower limit of the content of talc is, for example, 15% by weight or less, and preferably 10% by weight or less, from the viewpoint of improving dispersion of inorganic powder in the topical composition to improve preparation stability. Specific ranges of the content of talc are 3 to 15% by weight, 3 to 10% by weight or less, 5 to 15% by weight, and 5 to 10% by weight or less.

Also, when talc is blended with the component (B), the lower limit of the ratio of talc per 100 parts by weight of the component (A) is, for example, 6 parts by weight or more, and preferably 13 parts by weight or more, from the viewpoint of preferably obtaining separation suppression and coloration suppression. The upper limit of the ratio of talc per 100 parts by weight of the component (A) is, for example, 35 parts by weight or less, and preferably 20 parts by weight or less, from the viewpoint of improving dispersion of inorganic powder in the topical composition to improve preparation stability. Specific ranges of the ratio of talc per 100 parts by weight of the component (A) are 6 to 35 parts by weight, 6 to 20 parts by weight, 13 to 35 parts by weight, and 13 to 20 parts by weight.

In the first topical composition in which zinc oxide is blended with the component (B), the lower limit of the content of zinc oxide is, for example, 4% by weight or more, preferably 5% by weight or more, and further preferably 10% by weight or more, from the viewpoint of more preferably obtaining separation suppression and coloration suppression. Further, the upper limit of the zinc oxide content is, for example, 40% by weight or less, preferably 20% by weight or less, and more preferably 15% by weight or less, from the viewpoint of smoothing properties of the topical composition without solidifying. Specific ranges of the content of the component (B) are 4 to 40% by weight, 4 to 20% by weight, 5 to 40% by weight, 5 to 20% by weight, 10 to 40% by weight, and 10 to 20% by weight.

Furthermore, in the first topical composition in which zinc oxide is blended with the component (B), the lower limit of the ratio of zinc oxide per 100 parts by weight of the component (A) is, for example, 15 parts by weight or more, and preferably 20 parts by weight or more, from the viewpoint of more preferably obtaining separation suppression and coloration suppression. The upper limit of the ratio of zinc oxide per 100 parts by weight of the component (A) is 45 parts by weight or less, and preferably 30 parts by weight or less, from the viewpoint of smoothing properties of the topical composition without being too hard. Specific ranges of the ratio of zinc oxide per 100 parts by weight of the component (A) are 15 to 45 parts by weight, 15 to 30 parts by weight, 20 to 45 parts by weight, and 20 to 30 parts by weight.

(C) Additive

The first topical composition of the present invention contains a specific additive as the component (C) together with the component (B). The second topical composition of the present invention can contain a specific additive as the component (C) together with the component (B). The component (C) is blended together with the component (B), thereby acting as a suppressor of separation and coloration in the topical composition containing the components (A) and (D).

The component (C) is selected from the group consisting of (c1) a cellulose derivative; (c2) a polyvinyl-type alcohol; and (c3) polyoxyethylene polyoxypropylene glycol. As the component (C), one of the component (c1), the component (c2), and the component (c3) may be used alone, or in combination of two or more types.

The content of the component (C) (the total amount of the component (c1), the component (c2) and the component (c3)) is not particularly limited, and it can be appropriately determined according to the type of the component (B), the type of the component (C), and separation suppression and coloration suppression to be exerted, and/or feeling of use. For example, the lower limit of the content of the component (C) is, 0.02% by weight or more, and preferably 0.05% by weight or more, from the viewpoint of preferably obtaining suppression of separation with time and suppression of coloration with time. Moreover, the upper limit of the content of the component (C) is 15% by weight or less, and preferably 12% by weight or less, from the viewpoint of obtaining good feeling of use. Specific contents of the component (C) are 0.02 to 15% by weight, 0.02 to 12% by weight, 0.05 to 15% by weight, and 0.05 to 12% by weight. These contents of the component (C) are particularly suitable in the first topical composition.

Further, in the second topical composition, the lower limit of the content of the component (C) is, for example, 0.02% by weight or more, and preferably 0.05% by weight or more, from the viewpoint of preferably obtaining suppression of separation with time and suppression of coloration with time. Furthermore, the upper limit of the content of the component (C) is, for example, 0.15 parts by weight or less, and preferably 0.1 parts by weight or less, from the viewpoint of obtaining good feeling of use. Specific contents of the component (C) in the second topical composition are 0.02 to 0.15% by weight, 0.02 to 0.1% by weight, 0.05 to 0.15% by weight, and 0.05 to 0.1% by weight.

The ratio of the component (C) to the component (A) is not particularly limited and is determined according to the contents of each of the component (C) and the component (A), but the lower limit of the ratio of the component (C) to 100 parts by weight of the component (A) is 0.1 parts by weight or more, from the viewpoint of preferably obtaining suppression of separation with time and suppression of coloration with time. Further, the upper limit of the ratio of the component (C) to 100 parts by weight of the component (A) is 25 parts by weight or less, and preferably 13 parts by weight or less, from the viewpoint of suppressing fluidity of the topical composition to obtain good feeling of use and/or more preferably obtaining separation suppression and coloration suppression. Specific ranges of the ratio of the component (C) to 100 parts by weight of the component (A) are 0.1 to 25 parts by weight and 0.1 to 13 parts by weight. These ratios of the component (C) are particularly suitable in the first topical composition.

In the second topical composition, the lower limit of the ratio of the component (C) to 100 parts by weight of the component (A) is 0.1 parts by weight or more. Moreover, the upper limit of the ratio of the component (C) to 100 parts by weight of the component (A) is 1.8 parts by weight or less, from the viewpoint of suppressing fluidity of the topical composition to obtain good feeling of use. A specific range of the ratio of the component (C) to 100 parts by weight of the component (A) in the second topical composition is 0.1 to 1.8 parts by weight.

Further, the total amount of the component (B) and the component (C) in the second topical composition is not particularly limited, and is determined by the contents of the component (B) and the component (C). The lower limit of the total amount of the component (B) and the component (C) is, for example, 3.5% by weight or more, and preferably 10% by weight or more, from the viewpoint of preferably obtaining separation suppression and coloration suppression of the topical composition. Moreover, the upper limit of the total amount of the component (B) and the component (C) is, for example, 14% by weight or less, and preferably 12.5% by weight or less, from the viewpoint of suppressing fluidity of the topical composition to obtain good feeling of use and/or preferably obtaining coloration suppression. Specific ranges of the contents of the component (B) and the component (C) are 3.5 to 14% by weight, 3.5 to 12.5 by weight, 10 to 14% by weight, and 10 to 12.5 by weight.

Furthermore, the lower limit of the ratio of the total amount of the component (B) and the component (C) per 100 parts by weight of the component (A) in the second topical composition is, for example, 9 parts by weight or more, and preferably 20 parts by weight or more, from the viewpoint of preferably obtaining separation suppression and coloration suppression of the topical composition.

The upper limit of the ratio of the total amount of the component (B) and the component (C) per 100 parts by weight of the component (A) is, for example, 60 parts by weight or less, and preferably 30 parts by weight or less, from the viewpoint of suppressing fluidity of the topical composition to obtain good feeling of use and/or preferably obtaining coloration suppression. Specific ranges of the total amount of the component (B) and the component (C) per 100 parts by weight of the component (A) are 9 to 60 parts by weight, 9 to 30 parts by weight, 20 to 60 parts by weight, and 20 to 30 parts by weight.

(c1) Cellulose Derivative

The cellulose derivative in the topical composition of the present invention is a cellulose derivative in which the hydroxyl group of cellulose is substituted with a substituent selected from the group consisting of —$OR^1$ group, —$OR^2OH$ group, —$OR^3OR^4$ group, and —$OCOR^5$ group. $R^1$ represents an alkyl group having 1 to 3 carbon atoms, and preferably represents a methyl group or an ethyl group. $R^2$ represents an alkylene group having 2 to 3 carbon atoms, and preferably represents —$CH_2$—$CH(CH_3)$— group or —$CH_2$—$CH_2$— group. $R^3$ represents 1 to 3 carbon atoms, preferably —$CH_2$—$CH(CH_3)$— group or —$CH_2$—$CH_2$— group, and more preferably —$CH_2$—$CH_2$— group. $R^4$ represents an alkyl group having 1 to 3 carbon atoms, preferably a methyl group or an ethyl group, and more preferably a methyl group. $R^5$ represents an organic group, and is preferably an alkyl group having 1 to 6 and preferably 1 to 3 carbon atoms; an aryl group having 6 to 12 and preferably 6 carbon atoms and a carboxyl group; an alkyl group having 2 to 6 and preferably 2 to 4 carbon atoms and a carboxyl group or the like, and is more preferably a group so that —$COR^5$ group serves as a monovalent acyl group such as an acetyl group (—$COCH_3$), or a divalent acyl group such as a phthaloyl group (—CO—$C_6H_4$—$CO_2H$) or a succinyl group (—CO—$CH_2CH_2$—$CO_2H$), or the like. One of these substituents may be contained alone, or a plurality of types may be contained in combination. In addition, at least a part of the hydroxyl groups of cellulose may be substituted with the substituent. Further, the cellulose derivative may be used alone, or in combination of two or more types. Furthermore, when the topical composition of the present invention contains a cellulose derivative, it is more preferable to further contain the component (E) described later, from the viewpoint of more favorably obtaining separation suppression and coloration suppression.

Specifically, the component (b1) can be selected from the group consisting of methylcellulose, ethylcellulose, hypromellose, hydroxyethylcellulose, hydroxypropyl cellulose, methyl hydroxyethyl cellulose, and an esterified product thereof. These cellulose derivatives are preferable in that suppression of separation with time is more favorably obtained.

The component (b1) is more preferably selected from the group consisting of hypromellose, methylcellulose, and an esterified product thereof in that suppression of separation with time is further favorably obtained. Further, hypromellose and/or methylcellulose is preferable as the component (c1), from the viewpoint of more preferably obtaining suppression of coloration with time. Hereinafter, these preferable celluloses (hypromellose, methylcellulose, and an esterified product thereof) will be described in more detail.

Hypromellose is also referred to as hydroxypropyl methylcellulose (HPMC). Hypromellose is a mixed ether of methyl and hydroxypropyl of cellulose. The type of degree of substitution of hypromellose used in the present invention is not particularly limited, and examples thereof include 1828, 2208, 2906, and 2910. These hypromellose may be used alone or in combination of two or more types. Hypromellose preferably includes the type of degree of substitution of 2906 and 2910, from the viewpoint of more favorably obtaining suppression of separation with time and suppression of coloration with time.

Methylcellulose is a methyl ether of cellulose. The degree of substitution of a methoxy group of methylcellulose used in the present invention as measured by a method based on methylcellulose quantification method in the 17th revised Japanese Pharmacopoeia is, for example, 26.0 to 33.0% by weight, and more preferably 27.5 to 31.5% by mass.

In addition, examples of the esterified product of hypromellose or methylcellulose include hypromellose phthalate (HPMCP), hypromellose acetate succinate (HPMCAS), methylcellulose phthalate, and the like. These esterified products may be used alone or in combination of two or more types. Among them, hypromellose phthalate (HPMCP) is preferable from the viewpoint of more favorably obtaining suppression of separation with time and suppression of coloration with time.

Hypromellose phthalate (HPMCP) is a monophthalate ester of hypromellose. The type of degree of substitution of hypromellose phthalate is not particularly limited, and examples thereof include 220824 and 200731. These hypromellose phthalates may be used alone or in combination of two or more types. Hypromellose phthalate preferably includes the type of degree of substitution of 220824, from the viewpoint of more favorably obtaining suppression of separation with time and suppression of coloration with time.

The molecular weight of each of the methylcelluloses used in the present invention is not particularly limited, and examples thereof include a weight average molecular weight of 10,000 to 500,000, preferably 100,000 to 500,000, and further preferably 300,000 to 500,000. The weight average molecular weight refers to the weight average molecular weight in terms of polyethylene glycol measured by gel permeation chromatography.

Viscosity grade of the component (c1) used in the present invention is not particularly limited. In the present invention, the viscosity grade of the component (c1) refers to viscosity of a predetermined concentration solution at 20° C., and the predetermined concentration solution refers to a solution of 2% by weight in water, in a case of a cellulose derivative in which a hydroxyl group of cellulose is substituted with —$OR^1$ group, —$OR^2OH$ group, and/or —$OR^3OR^4$ group, and refers to a solution of 10% by weight in a methanol-dichloromethane mixed solution (1:1 weight ratio) when the hydroxyl group of cellulose is substituted with —$OCOR^5$ group (that is, it is an esterified product). In addition, the viscosity of the predetermined concentration solution is in accordance with the description of the 17th revised Japanese Pharmacopoeia, and refers to a value measured by the first method (capillary viscometer method) of the 17th revised Japanese Pharmacopoeia "2.53 Viscosity Measurement Method" for those of less than 600 mPa·s, and refers to a value measured by the second method (rotational viscometer method) for those of 600 mPa·s or more.

For example, a sum of products of a viscosity grade of each of the components (c1) and a weight ratio when total components (c1) (hereinafter, may be described as "average value of the viscosity grade" of the component (c1)) may be 50 mPa·s or more or may be less than 50 mPa·s. When, for example, a component having a viscosity grade of $\eta_1$ (mPa·s) is used alone as the component (c1), the average value of the viscosity grade of the component (c1) is $\eta_1$ (mPa·s). When, for example, hypromellose having a viscosity grade of $\eta_2$ (mPa·s) and hypromellose phthalate having a viscosity grade of $\eta_3$ (mPa·s) are used at a weight ratio of 1:1 as the component (c1), the average value of the viscosity grade of the component (c1) is $0.5\ \eta_2 + 0.5\ \eta_3$ (mPa·s).

For example, the average value of the viscosity grade of the component (c1) is preferably 50 mPa·s or more, more preferably 60 mPa·s or more, further preferably 100 mPa·s or more, even more preferably 1500 mPa·s or more, and particularly preferably 4000 mPa·s or more, from the viewpoint of more favorably obtaining separation suppression. The upper limit of the average value of the viscosity grade of the component (c1) is not particularly limited, but is, for example, 10,000 mPa·s or less, from the viewpoint of favorably obtaining good feeling of use by improving extensibility and/or suppressing spinning. That is, specific ranges of the average value of the viscosity grade of the component (c1) are 50 to 10000 mPa·s, 60 to 10000 mPa·s, 100 to 10000 mPa·s, 1500 to 10000 mPa·s, and 4000 to 10000 mPa·s. The average value of the viscosity grades of the component (c1) is particularly preferable when the component (c3) is not contained as the component (C).

Further, when the average value of the viscosity grade of the component (c1) is 50 mPa·s or more and it is used in combination with the component (c3), it is preferable that a surfactant other than the component (c3) is further used in combination and/or it is blended so that the total amount of the component (C) is equal to or above a predetermined value, specifically 5.9% by weight or more, more specifically, 5.9 to 15% by weight, and preferably 5.9 to 12% by weight, from the viewpoint of more favorably obtaining separation suppression.

In the present invention, desired separation suppression can be obtained even when the average value of the viscosity grade of the component (c1) is less than 50 mPa·s, but more favorable separation suppression can also be obtained by using in combination with at least one of the component (c1) with a higher viscosity grade, other thickener, and the component (c3). The component (c1) with a higher viscosity grade has a viscosity grade of 50 mPa·s or more, more preferably 60 mPa·s or more, further preferably 100 mPa·s or more, even more preferably 1500 mPa·s or more, and particularly preferably 4000 mPa·s or more. The upper limit of the viscosity grade of the component (c1) with a higher viscosity grade is not particularly limited, but is, for example, 10000 mPa·s or less, from the viewpoint of favorably obtaining good feeling of use by improving extensibility and/or suppressing spinnability. That is, specific ranges of the viscosity grade of the component (c1) with a high viscosity grade are 50 to 10000 mPa·s, 60 to 10000 mPa·s, 100 to 10000 mPa·s, 1500 to 10000 mPa·s, and 4000 to 10000 mPa·s.

Among these, it is more preferable to use it in combination with the component (c3) from the viewpoint of even more favorably obtaining suppression of coloration with time. In this case, the component (c3) can be used, for example, in an amount of 1 to 120 parts by weight, and preferably 3 to 120 parts by weight, based on 1 part by weight of the component (c1), from the viewpoint of more favorably obtaining suppression of separation with time. When used in combination with other thickener, examples of the other thickener include starch from the viewpoint of suppression of coloration with time. In this case, the other thickener can be used, for example, in an amount of 0.5 to 10 parts by weight, and preferably 1 to 5 parts by weight, based on 1 part by weight of the component (c1), from the viewpoint of more favorably obtaining suppression of separation with time and suppression of coloration with time. When the average value of the viscosity grade of the component (c1) is less than 50 mPa·s, the lower limit of the average value of the viscosity grade of the component (c1) is not particularly limited as long as separation suppression is obtained, but is, for example, 3 mPa·s or more. That is, when the average value of the viscosity grade of the component (c1) is less than 50 mPa·s, a specific range of the average value of the viscosity grade of the component (c1) is 3 to 50 mPa·s.

The amount of the component (c1) in the topical composition of the present invention is not particularly limited, and can be appropriately determined depending on separation suppression and coloration suppression to be exerted, and/or feeling of use. For example, the lower limit of the content of the component (c1) in the first topical composition is, for example, 0.05% by weight or more, and preferably 0.1% by weight or more as the total amount of the component (c1), from the viewpoint of favorably obtaining suppression of separation with time and suppression of coloration with time. Further, the upper limit of the content of the component (c1) is, for example, 8% by weight or less, preferably 5% by weight or less, and more preferably 2 parts by weight or less, from the viewpoint of obtaining good feeling of use. Specific ranges of the content of the component (c1) in the first topical composition are 0.05 to 8% by weight, 0.05 to 5% by weight, 0.05 to 2% by weight, 0.1 to 8% by weight, 0.1 to 5% by weight, and 0.1 to 2% by weight. These contents of the component (c1) are particularly suitable in the first topical composition.

Furthermore, the ratio of the component (c1) to the component (A) in the first topical composition is not particularly limited, but the lower limit of the total amount of the component (c1) per 100 parts by weight of the total amount of the component (A) is, for example, 0.8 parts by weight or more, and preferably 1 part by weight or more, from the viewpoint of favorably obtaining suppression of separation with time and suppression of coloration with time. The upper limit of the total amount of (c1) per 100 parts by weight of the total amount of the component (A) is, for example, 25 parts by weight or less, from the viewpoint of obtaining good feeling of use. Specific ranges of the total amount of the component (c1) per 100 parts by weight of the total amount of the component (A) in the first topical composition are 0.8 to 25 parts by weight and 1 to 25 parts by weight. These ratios of the components (c1) are particularly suitable in the first topical composition.

Further, the lower limit of the content of the component (c1) in the second topical composition is 0.02% by weight or more, and preferably 0.05% by weight or more, from the viewpoint of preferably obtaining separation suppression and suppression of coloration with time. Moreover, the upper limit of the content of the component (c1) is, for example, 0.3% by weight or less, preferably 0.15% by weight or less, and more preferably 0.1% by weight or less, from the viewpoint of suppressing fluidity of the topical composition to obtain good feeling of use. The above upper limit is particularly suitable when titanium oxide is contained in an amount of 3% by weight or more as the component (B). Specific contents of the component (c1) in the second topical composition are 0.02 to 0.3% by weight, 0.02 to 0.15% by weight, 0.02 to 0.1% by weight, 0.05 to 0.3% by weight, 0.05 to 0.15% by weight, and 0.05 to 0.1% by weight.

Furthermore, the lower limit of the total amount of (c1) per 100 parts by weight of the total amount of the component (A) in the second topical composition is, for example, 0.05 parts by weight or more, and preferably 0.1 parts by weight or more, from the viewpoint of favorably obtaining suppression of separation with time and suppression of coloration with time. The upper limit of the content of (c1) per 100 parts by weight of the total amount of the component (A) is, for example, 1.7 parts by weight or less, preferably 1.2 parts by weight or less, more preferably 0.5 parts by weight, and further preferably 0.3 parts by weight or less, from the viewpoint of obtaining good feeling of use. The above upper limit is particularly suitable when titanium oxide is contained as the component (B) in an amount of 6 parts by weight or more per 100 parts by weight of the component (A). Specific ranges of the total amount of (c1) per 100 parts by weight of the total amount of the component (A) in the second topical composition are 0.05 to 1.7 parts by weight, 0.05 to 1.2 parts by weight, 0.05 to 0.5 parts by weight, 0.05 to 0.3 parts by weight, 0.1 to 1.7 parts by weight, 0.1 to 1.2 parts by weight, 0.1 to 0.5 parts by weight, and 0.1 to 0.3 parts by weight.

(c2) Polyvinyl-Type Alcohol

The polyvinyl-type alcohol in the topical composition of the present invention is selected from the group consisting of polyvinyl alcohol (PVA) and a derivative thereof. These polyvinyl-type alcohols are known components as thickeners. Among the components (C), the polyvinyl-type alcohol are preferable in that suppression of coloration with time is more favorably obtained. When the topical composition of the present invention contains the polyvinyl-type alcohol, it is more preferable to further contain the component (E) described later, from the viewpoint of more favorably obtaining the effect of the present invention. As the polyvinyl-type alcohol, one type from polyvinyl alcohol and a derivative thereof may be used alone, or two or more may be used in combination.

Polyvinyl alcohol (PVA) refers to a completely saponified product of polyvinyl acetate. Examples of the derivative of polyvinyl alcohol include partially saponified products of polyvinyl acetate, as well as various modified PVAs such as amine-modified PVA, ethylene-modified PVA, terminal thiol-modified PVA, and ethylene copolymer-modified PVA (EvOH). As the derivative of polyvinyl alcohol, one type may be used alone, or two or more may be used in combination. Among these, partially saponified products of PVA and polyvinyl acetate (PVA which is a partially saponified product) are preferable, from the viewpoint of more favorably obtaining suppression of separation with time and suppression of coloration with time. The degree of saponification of the partially saponified product of polyvinyl acetate is preferably 60 mol % or more and less than 100 mol %, more preferably 78 to 96 mol %, and further preferably 85 to 90 mol %.

The degree of polymerization of polyvinyl alcohol and a derivative thereof is not particularly limited, but the average degree of polymerization measured in accordance with JIS K-6726 is, for example, 300 to 4500, preferably 400 to 4000, and more preferably 500 to 3500, from the viewpoint of more favorably obtaining suppression of separation with time.

The amount of (c2) in the topical composition of the present invention is not particularly limited, and the lower limit of the total amount of (c2) is 0.1% by weight, and preferably 1% by weight or more, from the viewpoint of favorably obtaining suppression of separation with time and suppression of coloration with time. The upper limit of the total amount of (c2) is 8% by weight or less, and preferably 5% by weight or less, from the viewpoint of obtaining good feeling of use. Specific ranges of the content of (c2) are 0.1 to 8% by weight, 0.1 to 5% by weight, 1 to 8% by weight, and 1 to 5% by weight.

Furthermore, the amount of (c2) to the component (A) is not particularly limited, but the lower limit of the ratio of (c2) per 100 parts by weight of the total amount of the component (A) is, for example, 0.16 parts by weight or more, and preferably 1.6 parts by weight or more, from the viewpoint of favorably obtaining suppression of separation with time and suppression of coloration with time. The upper limit of the ratio of (c2) per 100 parts by weight of the total amount of the component (A) is 13 parts by weight or less, and preferably 8 parts by weight or less, from the viewpoint of obtaining good feeling of use. Specific ranges of the ratio of (c2) per 100 parts by weight of the total amount of the component (A) are 0.16 to 13 parts by weight, 0.16 to 8 parts by weight, 1.6 to 13 parts by weight, and 1.6 to 8 parts by weight.

(c3) Polyoxyethylene Polyoxypropylene Glycol

The polyoxyethylene polyoxypropylene glycol in the topical composition of the present invention is a compound obtained by addition polymerization of ethylene oxide to polypropylene glycol obtained by addition polymerization of propylene oxide, and is a known component as a nonionic surfactant. Among the components (C), polyoxyethylene polyoxypropylene glycol is preferable in that suppression of coloration with time is more favorably obtained. Moreover, since polyoxyethylene polyoxypropylene glycol is also excellent in function as an ointment base material, when the topical composition of the present invention contains polyoxyethylene polyoxypropylene glycol, the effect of the present invention can be favorably obtained even if the component (E) is not contained. In the following description, POE represents polyoxyethylene, POP represents polyoxypropylene, and the number in parentheses represents an addition molar number.

The average degree of polymerization of propylene oxide and ethylene oxide in POEPOP glycol is not particularly limited, and the average degree of polymerization of propylene oxide is, for example, 5 to 100, preferably 20 to 80, and more preferably 30 to 70. Further, the average degree of polymerization of ethylene oxide is, for example, 3 to 250, preferably 20 to 220, and more preferably 100 to 200. These POPPOE glycols include POE(196) POP(67) glycol (Poloxamer 407, average molecular weight 11500), POE(24) POP (20) glycol (Poloxamer 124, average molecular weight 2200), POE(160) POP(30) glycol (Poloxamer 188, average molecular weight 8350), POE(54) POP(39) glycol (Poloxamer 235, average molecular weight 4600), POE(200) POP (70) glycol, and the like. Among these, POE(160) POP(30) glycol is preferable from the viewpoint of preferably obtaining suppression of separation with time and suppression of coloration with time.

The amount of (c3) in the topical composition of the present invention is not particularly limited, and the lower limit of the total amount of (c3) is, for example, 0.5% by weight or more, and preferably 1% by weight, from the viewpoint of favorably obtaining suppression of separation with time and suppression of coloration with time. Moreover, the upper limit of the total amount of (c3) is 20% by weight or less, and preferably 15% by weight or less, from the viewpoint of favorably obtaining suppression of coloration with time. Specific ranges of the total amount of (c3) are 0.5 to 20% by weight, 0.5 to 15% by weight, 1 to 20% by weight, and 1 to 15% by weight.

Further, the amount of (c3) to the component (A) is not particularly limited, but the lower limit of the ratio of (c3) per 100 parts by weight of the total amount of the component (A) is, for example, 0.8 parts by weight or more, and preferably 6 parts by weight or more, from the viewpoint of favorably obtaining suppression of separation with time and suppression of coloration with time. Furthermore, the upper limit of the ratio of (c3) per 100 parts by weight of the total amount of the component (A) is, for example, 32 parts by weight or less, and preferably 19 parts by weight or less, from the viewpoint of favorably obtaining suppression of coloration with time. Specific ranges of the ratio of (c3) per 100 parts by weight of the total amount of the component (A) are 0.8 to 32 parts by weight, 0.8 to 19 parts by weight, 6 to 32 parts by weight, and 6 to 19 parts by weight.

(D) Solvent

The topical composition of the present invention contains a solvent as the component (D). The solvent includes organic solvents such as monohydric lower alcohols (for example, monohydric alcohols having 1 to 5 carbon atoms such as methanol, ethanol, n-propanol, and isopropyl alcohol) and acetone, and aqueous solvents (for example, physiological saline, water, etc.), and is preferably water. Although the topical composition of the present invention contains a solvent, it suppresses separation with time and also suppresses coloration with time.

The amount (total amount) of the component (D) in the topical composition of the present invention is, for example, 0.01 to 40% by weight, preferably 10 to 40% by weight, more preferably 20 to 30% by weight, and further preferably 23 to 27% by weight. These contents of the component (D) are particularly suitable in the first topical composition.

In the second topical composition, the amount (total amount) of the component (D) is, in addition to the above-mentioned amounts (0.01 to 40% by weight, preferably 10 to 40% by weight, more preferably 20 to 30% by weight, and further preferably 23 to 27% by weight), for example, 20 to 25% by weight, preferably 20 to 24% by weight, and more preferably 20 to 22% by weight.

(E) Polyethylene Glycol

As for polyethylene glycol, the topical composition of the present invention can further contain polyethylene glycol which is an aqueous substrate as the component (E). Polyethylene glycol is a component known as a water-soluble substrate, also called macrogol. Polyethylene glycol is also excellent as an ointment base.

The molecular weight of polyethylene glycol is not limited, but, for example, one having a weight average molecular weight of 100 to 50,000, and preferably 400 to 20,000 can be used. Examples thereof include Macrogol 400, Macrogol 1500, Macrogol 4000, Macrogol 6000, Macrogol 20000, and Macrogol ointment (equal weight mixture of Macrogol 400 and Macrogol 4000) listed in the 17th revised Japanese Pharmacopoeia. These polyethylene glycols may be used alone or in combination of two or more types. The weight average molecular weight refers to the weight average molecular weight in terms of polyethylene glycol measured by gel permeation chromatography.

When the topical composition of the present invention contains the component (E), the amount thereof is not particularly limited, and the total amount is, for example, 1 to 45% by weight, preferably 1 to 32% by weight, and more preferably 6 to 15% by weight, from the viewpoint of more favorably obtaining suppression of separation with time, and the like. These amounts of the component (E) are particularly suitable in the first topical composition.

In the second topical composition, the amount of the component (E) is, for example, 4 to 45% by weight, preferably 20 to 30% by weight, and more preferably 20 to 22% by weight.

(F) Polyhydric Alcohol

The topical composition of the present invention may further contain a polyhydric alcohol in order to improve feeling of use, etc. and to adjust viscosity appropriately at the time of use. The polyhydric alcohol is a substance known as an aqueous base or the like, and the feeling of use can be improved by imparting good extensibility and/or spinning suppression to the topical composition of the present invention.

The polyhydric alcohol is not particularly limited as long as it is pharmaceutically acceptable, and examples thereof include ethylene glycol, 1,3-butylene glycol, propylene glycol, isoprene glycol, diethylene glycol, dipropylene glycol, polypropylene glycol, glycerin, and the like. These polyhydric alcohols may be used alone or in combination of two or more types. Among these, glycerin is preferable from the viewpoint of further improving feeling of use by imparting better extensibility and/or spinning suppression to the topical composition of the present invention.

When the topical composition of the present invention contains the component (F), the content (total amount) thereof is not particularly limited, and the lower limit of the content of the component (F) is, for example, 0.05% by weight or more, preferably 0.1% by weight or more, and more preferably 1% by weight or more. The upper limit of the content of the component (F) is, for example, 30% by weight or less, preferably 10% by weight or less, and more preferably 5% by weight or less. Specific ranges of the content of the component (F) are 0.05 to 30% by weight, 0.05 to 10% by weight, 0.05 to 5% by weight, 0.1 to 30% by weight, 0.1 to 10% by weight, 0.1 to 5% by weight, 1 to 30% by weight, 1 to 10% by weight, and 1 to 5% by weight.

Surfactant

The topical composition of the present invention may further contain a surfactant other than polyoxyethylene polyoxypropylene glycol, from the viewpoint of further stabilizing the dispersed state to more favorably obtain a better separation suppressing effect with time, and the like. The surfactant is not particularly limited as long as it is pharmaceutically acceptable, and any of a nonionic surfactant (other than polyoxyethylene polyoxypropylene glycol), an anionic surfactant, a cationic surfactant, and an amphoteric surfactant may be used. Among these, anionic surfactants and/or nonionic surfactants are preferable from the viewpoint of more favorably obtaining a separation suppressing effect with time and/or a coloration preventing effect with time, and the like.

Examples of the anionic surfactant include alkyl sulfates such as sodium lauryl sulfate, N-acylsarcosinates such as sodium N-lauroylsarcosine and sodium N-myristylsarcosine, and N-acylglutamates such as sodium N-palmitoylglutamate, sodium N-methyl-N-acyltaurine, sodium N-methyl-N-acylalanine, sodium α-olefin sulfonate, and the like.

Examples of the nonionic surfactant include sugar fatty acid esters such as sucrose fatty acid esters and maltose fatty acid esters, sugar alcohol fatty acid esters such as maltitol fatty acid esters and lactitol fatty acid esters, polyglycerol fatty acid esters such as sorbitan fatty acid esters, glycerin fatty acid esters, hexaglyceryl monolaurate, hexaglyceryl monomyristate, decaglyceryl monolaurate and decaglyceryl monomyristate, polyoxyethylene sorbitan fatty acid esters such as polyoxyethylene sorbitan monolaurate and polyoxyethylene sorbitan monostearate, polyoxyethylene fatty acid esters such as polyoxyethylene hardened castor oil, polyoxyethylene higher alcohol ethers such as polyoxyethylene lauryl ether, fatty acid alkanolamides such as lauric acid diethanolamide, polyoxyethylene polyoxypropylene copolymers, polyoxyethylene polyoxypropylene fatty acid esters, and the like.

Examples of the cationic surfactant include alkylammonium, alkylbenzylammonium salts, and the like. Examples of the amphoteric surfactant include betaine-based surfactants such as alkyl betaine, fatty acid amide propyl betaine, alkylimidazolinium betaine, and the like. These surfactants may be used alone or in combination of two or more types.

When the topical composition of the present invention contains a surfactant (other than polyoxyethylene polyoxypropylene glycol), the amount thereof is not particularly limited, and the total amount is, for example, 0.1 to 10% by weight, preferably 0.1 to 5% by weight, and further preferably 0.1 to 1% by weight, from the viewpoint of more favorably obtaining suppression of separation with time and/or coloration preventing effect with time, and the like.

Other Components

In addition to the above-mentioned components, the topical composition of the present invention may contain other bases and additives usually used for topical preparations for skin and the like, if necessary. Such base materials and additives are not particularly limited as long as they are pharmaceutically acceptable, and examples thereof include oily bases such as oils (olive oil, safflower oil, soybean oil, camellia oil, corn oil, rapeseed oil, sunflower oil, cottonseed oil, peanut oil, lard, squalane, fish oil, etc.), mineral oils (liquid paraffin, paraffin, gelled hydrocarbon, vaseline, etc.), waxes (yellow beeswax, carnauba wax, candelilla wax, ceresin, rice wax, microcrystalline wax, etc.), ester oils (isopropyl myristate, isopropyl adipate, diethyl sebacate, isopropyl sebacate, isopropyl palmitate, cetyl palmitate, ethyl oleate, etc.), fatty acid alkyl esters, fatty acids (stearic acid, oleic acid, palmitic acid, behenic acid, linoleic acid, lanolin, etc.), fatty acid esters (cetyl palmitate, isopropyl palmitate, ethyl linoleate, etc.), higher alcohols (stearyl alcohol, cetanol, behenyl alcohol, myristyl alcohol, oleyl alcohol, hexadecyl alcohol, lanoline alcohol, etc.), cholesterol, glyceryl tri2-ethylhexanoate, cetyl 2-ethylhexanoate, and silicone oils (dimethylpolysiloxane, cyclic silicone, etc.); and additives such as flavoring agents (citral, 1,8-cineole, citronellal, farnesol, etc.), colorants (tar dyes (brown 201, blue 201, yellow 4, yellow 403, etc.), cacao pigments, chlorophyll, aluminum oxide, etc.), pH adjusters (phosphoric acid, hydrochloric acid, citric acid, sodium citrate, succinic acid, tartaric acid, sodium hydroxide, potassium hydroxide, triethanolamine, triisopropanolamine, etc.), wetting agents (dl-sodium pyrrolidone carboxylate solution, D-sorbitol solution, etc.), stabilizers (dibutylhydroxytoluene, butylhydroxyanisole, sodium edetate, sodium metaphosphate, L-arginine, L-aspartic acid, DL-alanine, glycine, sodium erythorbate, propyl gallate, sodium sulfite, sulfur dioxide, chlorogenic acid, catechin, rosemary extract, etc.), antioxidants, ultraviolet absorbents, chelating agents, pressure sensitive adhesives, buffers, solubilizing agents, solubilizers, and preservatives.

Properties, Preparation Form, etc.

Properties of the topical composition of the present invention are not particularly limited, and examples thereof include an aqueous liquid composition, an aqueous gel composition, an oil gel composition, an emulsified composition, and the like. Among these, the aqueous gel composition and the emulsified composition are preferable, and the aqueous gel composition is more preferable, from the viewpoint of preparation stability and ease of washing with water. Emulsified state of the emulsified composition may be either an oil-in-water type or a water-in-oil type, and the oil-in-water type is preferable from the viewpoint of ease of washing with water.

The preparation form of the topical composition of the present invention is not particularly limited, and examples thereof include ointments, creams and the like, from the viewpoint of applicability and retention on the skin. Moreover, specific embodiments of the topical composition of the present invention include topical pharmaceuticals.

The pH of the topical composition of the present invention is, for example, 1.5 to 3.5, preferably 2 to 3.0, and further preferably 2.5 to 3.0. Moreover, the viscosity of the topical composition of the present invention is 0.1 kPa·s or more, preferably 1 or more, and further preferably 5 kPa·s. The viscosity of the topical composition of the present invention is a value measured under the following conditions using a B-type viscometer, specifically, VISCOMETER TV-20 (TVH) (manufactured by Toki Sangyo Co., Ltd).

Conditions: Rotor H7, rotation speed 0.3 rpm, measurement range R, 25° C.

Further, the topical composition of the present invention may be an agent prepared before use or a commercially available preparation, but is particularly preferably a commercially available preparation because it is excellent in suppressing syneresis and coloration with time.

Use

The topical composition of the present invention is used by applying it to an affected area where bleeding or exudate is observed at a cancerous skin ulcer site. Such affected area has an extensive cancerous skin ulcer due to advanced skin cancer or cancers other than skin cancer exposed on the body surface (e.g., breast cancer, head and neck cancer, etc.), and bleeding or exudate is observed. The topical composition of the present invention can be used for the purpose of improving quality of life (QOL) against such bleeding or exudate at the cancerous skin ulcer site, or infection or foul smell caused by these. In addition, the topical composition of the present invention may be used for the purpose of reducing cancerous skin ulcers.

The topical composition of the present invention can be used, for example, in the same manner as in application of Mohs' method. Specifically, the topical composition of the present invention is applied to the surface of a cancerous skin ulcer to fix a tumor tissue. In the fixation of tumor tissue, the tumor tissue can be degenerated and necrosed by hardening a tumor blood vessel, and the necrotic tissue can be fixed and dried. After confirming the fixation of the tumor tissue, the applied topical composition can be removed if necessary.

Dosage and Administration

The topical composition of the present invention can be used in a dosage and administration according to the size of the affected area where bleeding or exudate is observed at the cancerous skin ulcer site and the degree of bleeding or exudate, and, for example, it can be used in dosage and administration based on the Mohs' method. For example, it can be applied to the affected area about once every 7 to 10 days for a period according to symptoms of the affected area.

Production Method

The topical composition of the present invention can be produced by a known method. For example, it can be produced by mixing and stirring a powder mixture in which solid components such as (A) zinc chloride, (B) inorganic powder and (C) additive are premixed, and a liquid component such as (D) solvent, or mixing and stirring a powder mixture in which solid components such as (A) zinc chloride, (B) inorganic powder and (C) additive are premixed, and a zinc chloride solution in which (B) zinc chloride is pre-dissolved in a liquid component such as (D) solvent.

2. Method for Suppressing Separation and Coloration

Furthermore, the present invention provides a method for suppressing separation and coloration in a topical composition containing 30 to 60% by weight of zinc chloride, zinc oxide and a solvent. Specifically, the method for suppressing separation and coloration of the present invention (hereinafter referred to as "the first method for suppressing separation and coloration") includes, in the topical composition, blending (B) inorganic powder and (C) additive together with (A) 30 to 60% by weight of zinc chloride and (D) solvent, in which the component (C) is selected from the group consisting of (c1) a cellulous derivative in which a hydroxyl group of cellulose is substituted with a substituent selected from the group consisting of —$OR^1$ group, —$OR^2OH$ group, —$OR^3OR^4$ group, and —$OCOR^5$ group ($R^1$ represents an alkyl group having 1 to 3 carbon atoms, $R^2$ represents an alkylene group having 2 to 3 carbon atoms, $R^3$ represents an alkylene group having 1 to 3 carbon atoms, $R^4$ represents an alkyl group having 1 to 3 carbon atoms, and $R^5$ represents an organic group); (c2) a polyvinyl-type alcohol selected from the group consisting of polyvinyl alcohol and a derivative thereof; and (c3) polyoxyethylene polyoxypropylene glycol, and the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate. That is, in the first method for suppressing separation and coloration of the present invention, (B) inorganic powder and (C) additive are used as a suppressor of separation and coloration.

The method for suppressing separation and coloration of the present invention (hereinafter, referred to as "the second method for suppressing separation and coloration") includes, in the topical composition, blending (B) inorganic powder together with (A) 30 to 60% by weight of zinc chloride and (D) solvent, in which the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate. That is, in the second method for suppressing separation and coloration of the present invention, (B) inorganic powder is used as a suppressor of separation and coloration.

In the method for suppressing separation and coloration of the present invention, the types and blending amounts of the components used, the preparation form, etc. of the topical composition are as described in the column of "1. Topical composition". Specifically, in the first method for suppressing separation and coloration of the present invention, the types and blending amounts of the components used, the preparation form, etc. of the topical composition are as described for the first topical composition in the column of "1. Topical composition". In addition, in the second method for suppressing separation and coloration of the present invention, the types and blending amounts of the components used, the preparation form, etc. of the topical composition are as described for the second topical composition in the column of "1. Topical composition".

EXAMPLES

Hereinafter, the present invention will be more specifically described with reference to Examples and Comparative Examples, but the present invention is not limited thereto.

Test Example 1

Table 1 shows details of additives and base materials used in the following examples and comparative examples. In Table 1, the viscosity grades (indicated as "viscosity" in the table) of HPMC (hypromellose) and methylcellulose are viscosity of a solution of 2% by weight in water, measured according to the method described in the column of hypromellose and methylcellulose of the 17th revised Japanese Pharmacopoeia, and the viscosity grade (indicated as "viscosity" in the table) of HPMCP (hypromellose phthalate) is viscosity of a solution of 10% by weight in a methanol-dichloromethane mixed solution (1:1 weight ratio), measured according to the method described in the column of hypromellose phthalate of the 17th revised Japanese Pharmacopoeia.

TABLE 1

| Labeling | Product name (generic name) | Grade · Type | Manufacturer |
| --- | --- | --- | --- |
| HPMC | TC-5 (hypromellose) | Type E, viscosity 3 mPa · s, degree of substitution 2910 | Shin-Etsu Chemical Co., Ltd. |
| HPMC(60SH-4000)2910 | METROSE (hypromellose) | Type 60SH4000, viscosity 4000 mPa · s, degree of substitution 2910 | Shin-Etsu Chemical Co., Ltd. |

TABLE 1-continued

| Labeling | Product name (generic name) | Grade · Type | Manufacturer |
|---|---|---|---|
| HPMC(65SH-4000)2906 | METROSE (hypromellose) | Type 65SH4000, viscosity 4000 mPa · s, degree of substitution 2906 | Shin-Etsu Chemical Co., Ltd. |
| HPMCP | HPMCP (hypromellose phthalate) | TypeHP50, viscosity 55 mPa · s, degree of substitution 200824 | Shin-Etsu Chemical Co., Ltd. |
| Methylcellulose (SM4000) | METROSE (methylcellulose) | Type SM4000, degree of substitution of methoxy group 26.0 to 33.0% by weight, viscosity 4000 mPa · s | Shin-Etsu Chemical Co., Ltd. |
| PVA (degree of polymerization 500) | Polyvinyl alcohol (degree of polymerization about 500) | Average degree of polymerization about 500, degree of saponification 86 to 90 mol % | Wako Pure Chemical Industries, Ltd. |
| PVA (degree of polymerization 3,500) | Polyvinyl alcohol 3,500 (derivative), partially saponified polyvinyl acetate | Average degree of polymerization about 3,500, degree of saponification 86 to 90 mol % | Wako Pure Chemical Industries, Ltd. |
| Starch | Starch, corn derived | Special grade reagent | Wako Pure Chemical Industries, Ltd. |
| Crystalline cellulose | CEOLUS PH101 (crystalline cellulose) | PH101 | Asahi Kasei Corporation |
| Alginic acid | KIMICA ALGIN ULV-20 (sodium alginate) | 10% viscosity 1800 to 2300 mPa · s | KIMICA Corporation |
| CMC | CMC Daicel (sodium carboxymethyl cellulose) | 1% viscosity 100 to 200 (mPa · s) degree of substitution: 0.6 to 0.8 | Daicel FineChem Ltd. |
| CMCNa(1330) | CMC Daicel (sodium carboxymethyl cellulose) | 1% viscosity 50 to 100 (mPa · s) degree of substitution: 1.0 to 1.5 | Daicel FineChem Ltd. |
| CMCNa(1350) | CMC Daicel (sodium carboxymethyl cellulose) | 1% viscosity 200 to 300 (mPa · s) degree of substitution: 1.0 to 1.5 | Daicel FineChem Ltd. |
| CMCNa(1380) | CMC Daicel (sodium carboxymethyl cellulose) | 1% viscosity 1000 to 2000 (mPa · s) degree of substitution: 1.0 to 1.5 | Daicel FineChem Ltd. |
| CMCNa(1390) | CMC Daicel (sodium carboxymethyl cellulose) | 1% viscosity 2500 to 4500 (mPa · s) degree of substitution: 1.0 to 1.5 | Daicel FineChem Ltd. |
| Polyacrylic acid | Polyacrylic acid 25,000 | Average molecular weight about 25,000 | Wako Pure Chemical Industries, Ltd. |
| ARONVIS AHX | ARONVIS AHX | 0.2% Aqueous solution of partially neutralized sodium polyacrylate | TOAGOSEI CO., LTD. |
| ARONVIS AHX AH-105X | ARONVIS AHX AH-105X | 0.2% Aqueous solution of partially neutralized sodium polyacrylate | TOAGOSEI CO., LTD. |
| ARONVIS AHX AH-106X | ARONVIS AHX AH-106X | 0.2% Aqueous solution of partially neutralized sodium polyacrylate | TOAGOSEI CO., LTD. |
| Propyleneglycol alginate | Propyleneglycol alginate | 150 mPa · s or more, Wako first grade | Wako Pure Chemical Industries, Ltd. |
| α-cyclodextrin | α-cyclodextrin | Wako first grade | Wako Pure Chemical Industries, Ltd. |
| Dextrin hydrate | Dextrin hydrate | For chemical | Wako Pure Chemical Industries, Ltd. |
| Xanthan gum | VIS TOP D-3000-C (xanthan gum) | | San-Ei Gen F.F.I., Inc. |
| Xanthan gum (acid resistance) | KELTROL CG-BT (Xanthan gum) | | Sansho Co., Ltd. |
| Poloxamer | Polyoxyethylene(160) polyoxypropylene(30) glycol | For biochemical | Wako Pure Chemical Industries, Ltd. |
| Na Lauryl sulfate | Sodium lauryl sulfate | For ion pair chromatography | Tokyo Chemical Industry Co., Ltd. |
| Polyoxyethylene lauryl ether | Polyoxyethylene(23) lauryl ether | For chemical | Wako Pure Chemical Industries, Ltd. |
| Polyoxyethylene hardened castor oil | Polyoxyethylene(10) hardened castor oil | | WAKO CHEMICAL, CO., LTD. |
| Macrogol 400 (PEG 400) | Polyethylene glycol 400 | Ph Eur Compliant product | Merck Corporation |

TABLE 1-continued

| Labeling | Product name (generic name) | Grade · Type | Manufacturer |
|---|---|---|---|
| Macrogol 4000 (PEG 4000) | Polyethylene glycol 4000 | Ph Eur Compliant product, flaky | Merck Corporation |
| Macrogol ointment | Macrogol ointment | Japanese Pharmacopoeia compliant, macrogol ointment | Yoshindo Inc. |

Topical compositions having compositions shown in Tables 2 to 4 were prepared. Specifically, they were prepared by mixing and stirring a powder mixture in which solid components such as zinc oxide, PEG4000 and HPMC were premixed, and a zinc chloride solution in which zinc chloride was pre-dissolved in a liquid agent such as water, PEG400 and glycerin. In Tables 2 to 4, the unit of numerical value indicating the amount of each component is % by weight. In a centrifuge tube (capacity: 15 mL) was filled 5 mL of each prepared topical composition, and separation suppression, coloration suppression, and feeling of use were evaluated.

(1) Separation Suppression

The centrifuge tube filled with 5 mL of each topical composition was centrifuged at 8000 rpm for 10 minutes, and separation processing was forcibly performed. The degree of separation suppression was evaluated on a scale of point 5 to 1, based on the following criteria. FIG. 1 schematically shows typical modes in which the degree of separation suppression is point 5 to 1 for the centrifuge tubes after centrifuging the topical compositions. In the centrifuge tube after centrifugation, the upper surface of the topical composition formed a slope as shown, and separation suppression was evaluated based on the presence or absence of separation of liquid from the topical composition, and the amount and fluidity of the separated liquid.

<Evaluation Criteria for Degree of Separation Suppression>
  5: No liquid separation is observed
  4: Liquid separation is slightly (the liquid level height of the liquid is lower than the midpoint of height that occupies the slope of the topical composition) observed, but the liquid does not flow even if the centrifuge tube is overturned
  3: Liquid separation is slightly (the liquid level height of the liquid is lower than the midpoint of height that occupies the slope of the topical composition) observed, and the liquid flows when the centrifuge tube is overturned
  2: Liquid separation is somewhat (the liquid level height of the liquid is higher than the midpoint of height that occupies the slope of the topical composition, and lower than near the peak of the height) observed, and the liquid flows when the centrifuge tube is overturned
  1: Liquid separation (the liquid level height of the liquid reaches near the peak of the height that occupies the slope of the topical composition) is much observed As the degree of separation suppression, 4 or more was used as an acceptance criterion for suppression of separation with time.

(2) Coloration Suppression

The centrifuge tube filled with 5 mL of each topical composition was stored in 60° C. environment for 7 days. After storage, the degree of coloration suppression was evaluated based on the following criteria.

<Evaluation Criteria for Degree of Coloration Suppression>
  ⊙: The degree of coloration is smaller than that of the macrogol formulation (Comparative Example 2).
  ○: The degree of coloration is the same as that of the macrogol formulation (Comparative Example 2).
  x: The degree of coloration is greater than that of the macrogol formulation (Comparative Example 2).

As the degree of coloration suppression, ○ or ⊙ was used as an acceptance criterion for suppression of coloration with time.

(3) Feeling of Use

The centrifuge tube filled with 5 mL of each topical composition was stored in a closed state at room temperature for 7 days, and then 2 g was taken out from 5 ml of the topical composition and spread on a plate. The degree of feeling of use (ease of handling) was evaluated based on the degree of stretch (spreadability) and spinnability, and the presence or absence of fluidity. Specifically, whether or not there was fluidity was first confirmed, and whether or not the topical composition was flowed out from a region on the plate surface where the topical composition was first spread was confirmed. Next, when there was no fluidity, feeling of use was evaluated from the viewpoint of spreadability and spinnability as compared with the starch formulation stored at room temperature for 7 days after preparation.

<Evaluation Criteria for Feeling of Use>
  ⊙: There is no fluidity, and spreadability is excellent, and spinnability is weaker than that of the starch formulation.
  ○: There is no fluidity, and spreadability and spinnability are equivalent to those of the starch formulations.
  Δ: There is no fluidity, spreadability is poor, and spinnability is stronger than that of the starch formulation.
  x: There is fluidity.

As the degree of feeling of use, ○ or ⊙ was used as an acceptable level for feeling of use. The composition of the starch formulation is 49% by weight zinc chloride, 12.3% by weight zinc oxide, 12.3% by weight starch, 2% by weight glycerin, and the balance is water.

TABLE 2

| | | Comparative Examples | | | | | | | | | | |
|---|---|---|---|---|---|---|---|---|---|---|---|---|
| | | 1 | 2 | 3 | 4 | 5 | 6 | 7 | 8 | 9 | 10 | 11 |
| (A) | Zinc chloride | 50 | 50 | 50 | 50 | 50 | 50 | 50 | 50 | 50 | 50 | 50 |
| (B) | Zinc oxide | 12.5 | 12.5 | 12.5 | 12.5 | 12.5 | 12.5 | 12.5 | 12.5 | 12.5 | 12.5 | 125 |
| (c1) | HPMC | | | | | | | | | | | |
| (c1) | HPMC (60SH-4000)2910 | | | | | | | | | | | |

TABLE 2-continued

| | | | | | | | | | | | | |
|---|---|---|---|---|---|---|---|---|---|---|---|---|
| (c1) | HPMC (65SH-4000)2906 | | | | | | | | | | | |
| (c1) | HPMCP | | | | | | | | | | | |
| (c1) | Methylcellulose (SM4000) | | | | | | | | | | | |
| (c2) | PVA (degree of polymerization 500) | | | | | | | | | | | |
| (c2) | PVA (degree of polymerization 3,500) | | | | | | | | | | | |
| | Starch | 5 | | | | | | | | | | |
| | Crystalline cellulose | | 3.125 | 3.125 | | | | | | | | |
| | Alginic acid | | | | 5 | | | | | | | |
| | CMC | | | | | 5 | | | | | | |
| | CMCNa (1330) | | | | | | 5 | | | | | |
| | CMCNa (1350) | | | | | | | 5 | | | | |
| | CMCNa (1380) | | | | | | | | 5 | | | |
| | CMCNa (1390) | | | | | | | | | 5 | | |
| | Polyacrylic acid | | | | | | | | | | 5 | |
| | ARONVIS AHX | | | | | | | | | | | 3.125 |
| | ARONVIS AHX-105X | | | | | | | | | | | |
| | ARONVIS AHX-106X | | | | | | | | | | | |
| | α-cyclodextrin | | | | | | | | | | | |
| | Dextrin hydrate | | | | | | | | | | | |
| | Propyleneglycol alginate | | | | | | | | | | | |
| | Xanthan gum | | | | | | | | | | | |
| | Xanthan gum (acid resistance) | | | | | | | | | | | |
| (c3) | Poloxamer | | | | | | | | | | | |
| | Na Lauryl sulfate | | 1 | | | | | | | | | |
| | Polyoxyethylene lauryl ether | | | | | | | | | | | |
| | Polyoxyethylene hardened castor oil | | | | | | | | | | | |
| (E) | Macrogol 400 (PEG 400) | 4.25 | 4.25 | 4.25 | 4.25 | 4.25 | 4.25 | 4.25 | 4.25 | 4.25 | 4.25 | 4.25 |
| (E) | Macrogol 4000 (PEG 4000) | 4.25 | 4.25 | 4.25 | 4.25 | 4.25 | 4.25 | 4.25 | 4.25 | 4.25 | 4.25 | 4.25 |
| (E) | Macrogol ointment | | | | | | | | | | | |
| (F) | Glycerin | 2.52 | 2.52 | 2.52 | 2.52 | 2.52 | 2.52 | 2.52 | 2.52 | 2.52 | 2.52 | 2.52 |
| (D) | Water | Balance | Balance | Balance | Balance | Balance | Balance | Balance | Balance | Balance | Balance | Balance |
| Total (% by weight) | | 100 | 100 | 100 | 100 | 100 | 100 | 100 | 100 | 100 | 100 | 100 |
| Separation suppression | | 3 | 2 | 3 | 2 | 3 | 2 | 2 | 2 | 1 | 2 | 2 |
| Coloration suppression | | ○ | Basis | ○ | ○ | ○ | ○ | ○ | ○ | ○ | ○ | ◎ |
| Feeling of use | | — | ○ | ◎ | Δ | ○ | Δ | Δ | Δ | Δ | Δ | Δ |

TABLE 2-continued

|  |  | Comparative Examples | | | | | | | | | |
|---|---|---|---|---|---|---|---|---|---|---|---|
|  |  | 12 | 13 | 15 | 16 | 17 | 18 | 19 | 20 | 21 | 22 |
| (A) | Zinc chloride | 50 | 50 | 50 | 50 | 50 | 50 | 50 | 50 | 50 | 50 |
| (B) | Zinc oxide | 12.5 | 125 | 125 | 12.5 | 12.5 | 12.5 | 12.5 | 2.5 | 12.5 | 12.5 |
| (c1) | HPMC |  |  |  |  |  |  |  |  |  |  |
| (c1) | HPMC(60SH-4000)2910 |  |  |  |  |  |  |  |  |  |  |
| (c1) | HPMC(65SH-4000)2906 |  |  |  |  |  |  |  |  |  |  |
| (c1) | HPMCP |  |  |  |  |  |  |  |  |  |  |
| (c1) | Methylcellulose (SM4000) |  |  |  |  |  |  |  |  |  |  |
| (c2) | PVA (degree of polymerization 500) |  |  |  |  |  |  |  |  |  |  |
| (c2) | PVA (degree of polymerization 3,500) |  |  |  |  |  |  |  |  |  |  |
|  | Starch |  |  |  |  |  |  |  |  |  |  |
|  | Crystalline cellulose |  |  |  |  |  |  |  |  |  |  |
|  | Alginic acid |  |  |  |  |  |  |  |  |  |  |
|  | CMC |  |  |  |  |  |  |  |  |  |  |
|  | CMCNa(1330) |  |  |  |  |  |  |  |  |  |  |
|  | CMCNa(1350) |  |  |  |  |  |  |  |  |  |  |
|  | CMCNa(1380) |  |  |  |  |  |  |  |  |  |  |
|  | CMCNa(1390) |  |  |  |  |  |  |  |  |  |  |
|  | Polyacrylic acid |  |  |  |  |  |  |  |  |  |  |
|  | ARONVIS AHX |  |  |  |  |  |  |  |  |  |  |
|  | ARONVIS AHX-105X | 3.125 |  |  |  |  |  |  |  |  |  |
|  | ARONVIS AHX-106X |  | 3.125 |  |  |  |  |  |  |  |  |
|  | α-cyclodextrin |  |  | 3.125 |  |  |  |  |  |  |  |
|  | Dextrin hydrate |  |  |  |  |  |  |  | 3.125 |  |  |
|  | Propyleneglycol alginate |  |  |  |  |  |  |  |  | 3.125 |  |
|  | Xanthan gum |  |  |  |  |  |  |  |  |  | 5 |
|  | Xanthan gum (acid resistance) |  |  |  |  |  |  |  |  |  |  |
| (c3) | Poloxamer |  |  |  |  |  |  |  |  |  |  |
|  | Na Lauryl sulfate |  |  |  |  |  |  |  |  |  |  |
|  | Polyoxyethylene lauryl ether |  |  |  | 3.125 |  |  |  |  |  |  |
|  | Polyoxyethylene hardened castor oil |  |  |  |  | 3.125 |  |  |  |  |  |
| (E) | Macrogol 400 (PEG 400) | 4.25 | 4.25 | 4.25 | 4.25 | 4.25 | 4.25 | 11.63 | 4.25 | 4.25 | 4.25 |
| (E) | Macrogol 4000 (PEG 4000) | 4.25 | 4.25 | 4.25 | 4.25 | 4.25 | 4.25 |  | 4.25 | 4.25 | 4.25 |
| (E) | Macrogol ointment |  |  |  |  |  |  |  |  |  |  |
| (F) | Glycerin | 2.52 | 2.52 | 2.52 | 2.52 | 2.52 | 5.645 | 2.52 | 2.52 | 2.52 | 2.52 |
| (D) | Water | Balance | Balance | Balance | Balance | Balance | Balance | Balance | Balance | Balance | Balance |
| Total (% by weight) |  | 100 | 100 | 100 | 100 | 100 | 100 | 100 | 100 | 100 | 100 |
| Separation suppression |  | 2 | 1 | 3 | 1 | 2 | 1 | 2 | 3 | 4 | 5 |
| Coloration suppression |  | ◎ | ◎ | ◎ | ◎ | ◎ | ◎ | ◎ | × | × | × |
| Feeling of use |  | Δ | Δ | Δ | Δ | Δ | Δ | Δ | Δ | Δ | Δ |

In the topical compositions of Comparative Example 1 (corresponding to the starch formulation of Non-Patent Document 1) and Comparative Example 2 (corresponding to the macrogol formulation of Non-Patent Document 3), spinnability was strong and the feeling of use was poor. Further, in the topical composition of Comparative Example 2, coloration was observed in addition to separation with time. In the topical compositions of Comparative Examples 3 to 14 in which various thickeners were blended, coloration with time was suppressed, but separation could not be suppressed yet. A similar tendency was observed in the topical compositions of Comparative Examples 15 to 16 in which the nonionic surfactant was blended, and coloration with time was suppressed in these topical compositions, but separation could not be suppressed yet. Even in the topical compositions of Comparative Example 17 in which the amount of glycerin was increased and Comparative Example 18 in which the amount of polyethylene glycol was increased, instead of containing a thickener or a nonionic surfactant, coloration with time was suppressed, but separation could not be suppressed yet. In addition, in the topical composition of Comparative Example 19 in which dextrin hydrate was blended as a thickener, both separation and coloration with time were observed. Moreover, in the topical compositions of Comparative Example 20 in which propylene glycol alginate was blended as a thickener and Comparative Example 21 in which xanthan gum was blended as a thickener, separation with time could be suppressed, but coloration with time was observed this time.

TABLE 3

|  |  | Examples | | | | | | |
|---|---|---|---|---|---|---|---|---|
|  |  | 1 | 2 | 3 | 4 | 5 | 6 | 7 |
| (A) | Zinc chloride | 50 | 50 | 50 | 50 | 50 | 50 | 50 |
| (B) | Zinc oxide | 12.5 | 12.5 | 12.5 | 12.5 | 12.5 | 12.5 | 12.5 |
| (c1) | HPMC |  |  |  |  |  | 1.5 | 1.5 |
| (c1) | HPMC(60SH-4000)2910 | 2 | 5 |  |  |  |  |  |
| (c1) | HPMC(65 SH-4000)2906 |  |  | 0.5 |  |  |  |  |
| (c1) | HPMCP |  |  |  | 3.125 | 5 | 1.625 |  |
| (c1) | Methylcellulose (SM4000) |  |  |  |  |  |  |  |
| (c2) | PVA (degree of polymerization 500) |  |  |  |  |  |  |  |
| (c2) | PVA (degree of polymerization 3,500) |  |  |  |  |  |  |  |
|  | Starch |  |  |  |  |  |  | 1.625 |
|  | Crystalline cellulose |  |  |  |  |  |  |  |
|  | Alginic acid |  |  |  |  |  |  |  |
|  | CMC |  |  |  |  |  |  |  |
|  | CMCNa(1330) |  |  |  |  |  |  |  |
|  | CMCNa(1350) |  |  |  |  |  |  |  |
|  | CMCNa(1380) |  |  |  |  |  |  |  |
|  | CMCNa(1390) |  |  |  |  |  |  |  |
|  | Polyacrylic acid |  |  |  |  |  |  |  |
|  | ARONVIS AHX |  |  |  |  |  |  |  |
|  | ARONVIS AH-105X |  |  |  |  |  |  |  |
|  | ARONVIS AHX-106X |  |  |  |  |  |  |  |
|  | α-cyclodextrin |  |  |  |  |  |  |  |
|  | Dextrin hydrate |  |  |  |  |  |  |  |
|  | Propyleneglycol alginate |  |  |  |  |  |  |  |
|  | Xanthan gum |  |  |  |  |  |  |  |
|  | Xanthan gum (acid resistance) |  |  |  |  |  |  |  |
| (c3) | Poloxamer |  |  |  |  |  |  |  |
|  | Na Lauryl sulfate |  |  |  |  |  |  |  |
|  | Polyoxyethylene lauryl ether |  |  |  |  |  |  |  |
|  | Polyoxyethylene hardened castor oil |  |  |  |  |  |  |  |
| (E) | Macro gol 400 (PEG 400) | 4.25 | 3.3125 | 4.25 | 4.25 | 4.25 | 4.25 | 4.25 |
| (E) | Macro gol 4000 (PEG 4000) | 4.25 | 3.3125 | 4.25 | 4.25 | 4.25 | 4.25 | 4.25 |
| (E) | Macrogol ointment |  |  |  |  |  |  |  |
| (F) | Glycerin | 2.52 | 2.52 | 2.52 | 2.52 | 2.52 | 2.52 | 2.52 |
| (D) | Water | Balance | Balance | Balance | Balance | Balance | Balance | Balance |
| Total (% by weight) |  | 100 | 100 | 100 | 100 | 100 | 100 | 100 |
| Separation suppression |  | 5 | 5 | 5 | 5 | 5 | 4 | 5 |
| Coloration suppression |  | ⊚ | ⊚ | ⊚ | ○ | ○ | ○ | ○ |
| Feeling of use |  | ⊚ | ○ | ⊚ | ⊚ | ⊚ | ⊚ | ⊚ |

|  |  | Examples | | | | | |
|---|---|---|---|---|---|---|---|
|  |  | 8 | 9 | 10 | 11 | 12 | 13 |
| (A) | Zinc chloride | 50 | 50 | 50 | 50 | 50 | 50 |
| (B) | Zinc oxide | 12.5 | 12.5 | 12.5 | 12.5 | 12.5 | 12.5 |
| (c1) | HPMC | 1 | 1 |  |  |  |  |
| (c1) | HPMC(60SH-4000)2910 |  |  |  |  |  |  |
| (c1) | HPMC(65 SH-4000)2906 |  |  |  |  |  |  |
| (c1) | HPMCP |  |  |  |  |  |  |
| (c1) | Methylcellulose (SM4000) |  |  |  | 0.5 |  |  |
| (c2) | PVA (degree of polymerization 500) |  |  |  |  | 3.125 |  |
| (c2) | PVA (degree of polymerization 3,500) |  |  |  |  |  |  |
|  | Starch |  |  |  |  |  |  |
|  | Crystalline cellulose |  |  |  |  |  |  |
|  | Alginic acid |  |  |  |  |  |  |
|  | CMC |  |  |  |  |  |  |
|  | CMCNa(1330) |  |  |  |  |  |  |
|  | CMCNa(1350) |  |  |  |  |  |  |
|  | CMCNa(1380) |  |  |  |  |  |  |
|  | CMCNa(1390) |  |  |  |  |  |  |
|  | Polyacrylic acid |  |  |  |  |  |  |
|  | ARONVIS AHX |  |  |  |  |  |  |
|  | ARONVIS AH-105X |  |  |  |  |  |  |
|  | ARONVIS AHX-106X |  |  |  |  |  |  |
|  | α-cyclodextrin |  |  |  |  |  |  |
|  | Dextrin hydrate |  |  |  |  |  |  |
|  | Propyleneglycol alginate |  |  |  |  |  |  |

TABLE 3-continued

|   | | | | | | | |
|---|---|---|---|---|---|---|---|
| | Xanthan gum | | | | | | |
| | Xanthan gum (acid resistance) | | | | | | |
| (c3) | Poloxamer | 4 | 5.3125 | | | 11.625 | 5.313 |
| | Na Lauryl sulfate | | | | | | |
| | Polyoxyethylene lauryl ether | | | | | | |
| | Polyoxyethylene hardened castor oil | | | | | | |
| (E) | Macro gol 400 (PEG 400) | 4.25 | | 4.25 | 4.25 | | |
| (E) | Macro gol 4000 (PEG 4000) | 4.25 | | 4.25 | 4.25 | | |
| (E) | Macrogol ointment | | 5.3125 | | | | 5.313 |
| (F) | Glycerin | 2.52 | 2.52 | 2.52 | 2.52 | 2.52 | 2.52 |
| (D) | Water | Balance | Balance | Balance | Balance | Balance | Balance |
| | Total (% by weight) | 100 | 100 | 100 | 100 | 100 | 100 |
| | Separation suppression | 4 | 5 | 5 | 4 | 4 | 4 |
| | Coloration suppression | ⊚ | ⊚ | ⊚ | ⊚ | ⊚ | ⊚ |
| | Feeling of use | ⊚ | ⊚ | ⊚ | ○ | ⊚ | ⊚ |

On the other hand, in Examples 1 to 13 containing hypromellose (HPMC), hypromellose phthalate (HPMCP) or methylcellulose as the (c1) component; polyvinyl alcohol as the (c2) component; or poloxamer (polyoxyethylene polyoxypropylene glycol) as the (c3) component, both separation with time and coloration with time could be suppressed.

Among the topical compositions of Examples 1 to 6 and 10 containing only the component (c1) and not containing the component (c3), in the topical compositions of Examples 1 to 3 (the average value of specific viscosity grades was 4000 mPa·s), Examples 4 to 5 (the average value of specific viscosity grades was 55 mPa·s) and Example 10 (the average value of specific viscosity grades was 4000 mPa·s), in which, a sum of products of a viscosity grade (viscosity of the 2% by weight solution at 20° C.) of the component (c1), that is, the viscosity grade, and a weight ratio when total components (c1) was 1 is 50 mPa·s or more, separation suppression tended to be superior to that of Example 6 in which the average value of viscosity grades was less than 50 mPa·s (the average value of specific viscosity grades was 30 mPa·s).

Further, when the average value of the viscosity grade of the component (c1) is less than 50 mPa·s, it was found that separation suppression was improved by combining the component (c1) with a high viscosity grade as in the topical composition of Example 6, combining other thickeners as in the topical composition of Example 7, or combining a poloxamer (polyoxyethylene polyoxypropylene glycol) as in the topical compositions of Examples 8 to 9, and among these, it is preferable to combine a poloxamer (polyoxyethylene polyoxypropylene glycol) in that coloration suppression could be also favorably obtained as shown in the topical compositions of Examples 8 to 9. In addition, as shown in the topical compositions of Examples 12 to 13, it was found that separation suppression and coloration suppression were obtained by blending a poloxamer (polyoxyethylene polyoxypropylene glycol), even if the component (c1) was not contained.

TABLE 4

| | | Examples | | | | | | | |
|---|---|---|---|---|---|---|---|---|---|
| | | 15 | 16 | 17 | 18 | 19 | 20 | 21 | 22 |
| (A) | Zinc chloride | 50 | 50 | 50 | 50 | 50 | 50 | 50 | 50 |
| (B) | Zinc oxide | 12.5 | 12.5 | 12.5 | 12.5 | 12.5 | 12.5 | 12.5 | 12.5 |
| (c1) | HPMC | | | | | | | | |
| (c1) | HPMC(60SH-4000)2910 | | | | | | | | |
| (c1) | HPMC(65SH-4000)2906 | 0.5 | 0.5 | 0.3 | 0.3 | 0.3 | 0.3 | 0.1 | 0.1 |
| (c1) | HPMCP | | | | | | | | |
| (c1) | Methylcellulose (SM4000) | | | | | | | | |
| (c2) | PVA (degree of polymerization 500) | | | | | | | | |
| (c2) | PVA (degree of polymerization 3,500) | | | | | | | | |
| | Starch | | | | | | | | |
| | Crystalline cellulose | | | | | | | | |
| | Alginic acid | | | | | | | | |
| | CMC | | | | | | | | |
| | CMCNa (1330) | | | | | | | | |
| | CMCNa (1350) | | | | | | | | |
| | CMCNa (1380) | | | | | | | | |
| | CMCNa (1390) | | | | | | | | |
| | Polyacrylic acid | | | | | | | | |
| | ARONVIS AHX | | | | | | | | |
| | ARONVIS AHX-105X | | | | | | | | |
| | ARONVIS AHX-106X | | | | | | | | |
| | α-cyclodextrin | | | | | | | | |
| | Dextrin hydrate | | | | | | | | |
| | Propyleneglycol alginate | | | | | | | | |
| | Xanthan gum | | | | | | | | |
| | Xanthan gum (acid resistance) | | | | | | | | |

TABLE 4-continued

|   |   |   |   |   |   |   |   |   |
|---|---|---|---|---|---|---|---|---|
| (c3) | Poloxamer | | | 5.66 | 5.41 | 5.54 | 5.61 | 11.525 | 5.763 |
| | Na Lauryl sulfate | | | | | | | | |
| | Polyoxyethylene lauryl ether | | | | | | | | |
| | Polyoxyethylene hardened castor oil | | | | 0.5 | 0.25 | 0.1 | | |
| (E) | Macrogol 400 (PEG 400) | 11.125 | 13.645 | 5.66 | 5.41 | 5.54 | 5.61 | | 5.763 |
| (E) | Macrogol 4000 (PEG 4000) | | | | | | | | |
| (E) | Macrogol ointment | | | | | | | | |
| (F) | Glycerin | 2.52 | | 2.52 | 2.52 | 2.52 | 2.52 | 2.52 | 2.52 |
| (D) | Water | Balance | Balance | Balance | Balance | Balance | Balance | Balance | Balance |
| Total (% by weight) | | 100 | 100 | 100 | 100 | 100 | 100 | 100 | 100 |
| Separation suppression | | 5 | 5 | 5 | 5 | 5 | 5 | 5 | 4 |

| | | Examples | | | | | | |
|---|---|---|---|---|---|---|---|---|
| | | 23 | 24 | 25 | 26 | 27 | 28 | 29 |
| (A) | Zinc chloride | 50 | 50 | 50 | 50 | 50 | 50 | 50 |
| (B) | Zinc oxide | 12.5 | 12.5 | 12.5 | 12.5 | 12.5 | 12.5 | 12.5 |
| (c1) | HPMC | | | | | | | |
| (c1) | HPMC(60SH-4000)2910 | | | | | | | |
| (c1) | HPMC(65SH-4000)2906 | 0.1 | 0.1 | 0.1 | | | | |
| (c1) | HPMCP | | | | | | | |
| (c1) | Methylcellulose (SM4000) | | | | | | | |
| (c2) | PVA (degree of polymerization 500) | | | | | | | |
| (c2) | PVA (degree of polymerization 3,500) | | | | 3.125 | | | |
| | Starch | | | | | | | |
| | Crystalline cellulose | | | | | | | |
| | Alginic acid | | | | | | | |
| | CMC | | | | | | | |
| | CMCNa (1330) | | | | | | | |
| | CMCNa (1350) | | | | | | | |
| | CMCNa (1380) | | | | | | | |
| | CMCNa (1390) | | | | | | | |
| | Polyacrylic acid | | | | | | | |
| | ARONVIS AHX | | | | | | | |
| | ARONVIS AHX-105X | | | | | | | |
| | ARONVIS AHX-106X | | | | | | | |
| | α-cyclodextrin | | | | | | | |
| | Dextrin hydrate | | | | | | | |
| | Propyleneglycol alginate | | | | | | | |
| | Xanthan gum | | | | | | | |
| | Xanthan gum (acid resistance) | | | | | | | |
| (c3) | Poloxamer | 5.71 | 5.71 | 5.71 | | 3.125 | 5.813 | 5.813 |
| | Na Lauryl sulfate | 0.1 | | 0.1 | | | 0.5 | 1 |
| | Polyoxyethylene lauryl ether | | | | | | | |
| | Polyoxyethylene hardened castor oil | | 0.1 | 0.1 | | | | |
| (E) | Macrogol 400 (PEG 400) | 5.71 | 5.71 | 5.71 | 4.25 | 4.25 | | |
| (E) | Macrogol 4000 (PEG 4000) | | | | 4.25 | 4.25 | | |
| (E) | Macrogol ointment | | | | | | 5.813 | 5.813 |
| (F) | Glycerin | 2.52 | 2.52 | 2.52 | 2.52 | 2.52 | 2.52 | 2.52 |
| (D) | Water | Balance | Balance | Balance | Balance | Balance | Balance | Balance |
| Total (% by weight) | | 100 | 100 | 100 | 100 | 100 | 100 | 100 |
| Separation suppression | | 5 | 5 | 5 | 4 | 4 | 5 | 5 |

Similarly, also in the topical compositions of Examples 14 to 28, excellent separation suppression was obtained. It was also excellent in coloration suppression. In particular, in the topical compositions of Examples 14 and 15 containing only the component (c1) and not containing the component (c3), a sum of products of a viscosity grade (viscosity of the 2% by weight solution at 20° C.) of the component (c1), that is, the viscosity grade, and a weight ratio when total components (c1) was 1 was 50 mPa·s or more, and separation suppression was superior to that in Example 6, as in the above-mentioned topical compositions of Examples 1 to 6 and 10. Further, among the topical compositions of Examples 16 to 24 having an average value of the viscosity grade of the component (c1) of 50 mPa·s or more and containing the component (c3), it was found that, by further blending surfactant other than the component (c3) as in the topical compositions of Examples 17 to 19 and 22 to 24, or blending so that the total amount of the components (C) (total amount of the components (c1) to (c3)) was 5.9% by weight or more as in the topical compositions of Examples 16 and 20, separation suppression superior to that of the topical composition of Example 21 not containing other surfactants and having a total amount of the components (C) below 5.9% by weight.

Test Example 2

Topical compositions having compositions shown in Tables 5 to 8 were prepared. Specifically, they were prepared by mixing and stirring a powder mixture in which solid components such as zinc oxide, titanium oxide, silicon dioxide, PEG4000 and HPMC were premixed, and a zinc chloride solution in which zinc chloride was pre-dissolved in a liquid agent such as water, PEG400 and glycerin. In Tables 5 to 8, the unit of numerical value indicating the amount of each component is % by weight.

The obtained topical compositions were evaluated for separation suppression, coloration suppression and feeling of use, in the same manner as in Test Example 1. The results are shown in Tables 5 to 8.

Further, among the topical compositions having the compositions shown in Tables 5 to 8, for the topical compositions of Examples 33, 35, 39, 45, and 55, evaluations of more detailed feeling of use, appearance, etc. are shown in Table 9. For the more detailed feeling of use, (i) the presence or absence of fluidity, (ii) ease of spreading on vulnerable affected areas, and (iii) ease of handling based on spinnability were evaluated. For the appearance, (iv) ease of viewing the applied site and (v) ease of uniform mixing during preparation (preparation by manual mixing) were evaluated. Since the topical composition of the present invention is highly irritating, the item (i) above is evaluated from the viewpoint of suppressing adhesion to normal skin other than the affected area. Since the cancerous skin ulcer site, which is the application site of the topical composition of the present invention, is vulnerable, the item (ii) above is evaluated from the viewpoint of suppressing the patient's pain and deterioration of the affected area due to physical stimulation at the time spreading on a vulnerable applied site by a topical composition being not too hard and being easy to spread. Since it is difficult to handle when spinnability is strong, the item (iii) above is evaluated from the viewpoint of facilitating handling of the topical composition to reduce burden on the patient. The item (iv) above is evaluated from the viewpoint of ensuring application to the application site by facilitating discrimination between the applied site and the non-applied site. In clinical practice, ease of viewing the applied portion may not be required. The item (v) above is evaluated from the viewpoint of facilitating preparation of a topical composition in which the components are uniformly dispersed.

TABLE 5

| | | Examples | | | | | | | | | | | |
|---|---|---|---|---|---|---|---|---|---|---|---|---|
| | | 29 | 30 | 31 | 32 | 33 | 34 | 35 | 36 | 37 | 38 | 39 | 40 |
| (A) | Zinc chloride | 49.2 | 29.5 | 59 | 44.05 | 44.05 | 44.05 | 44.05 | 44.05 | 44.05 | 44.05 | 44.05 | 44.05 |
| (B) | Zinc oxide | 12.3 | 12.3 | 12.3 | | | | | | | | | |
| (B) | Silicon dioxide (*) | | | | 6 | 4 | 3.3 | 4 | 4.5 | 4.5 | 4.5 | 4.5 | 5 |
| (B) | Titanium oxide | | | | | | 6 | 6 | 6 | 6 | 6 | 6 | 6 |
| (B) | Talc | | | | | | | | | | | | |
| | Aluminum oxide | | | | | | | | | | | | |
| | Bentonite | | | | | | | | | | | | |
| (c1) | HPMC(60SH-4000)2910 | 0.492 | 0.5 | 0.5 | | | 0.492 | | | 0.1 | 0.2 | 0.492 | 0.1 |
| (c1) | HPMCP | | | | | | | | | | | | |
| (c3) | Poloxamer | | | | | | | | | | | | |
| (E) | Macrogol 400 (PEG 400) | 5.47 | 15.3 | 0.6 | 13.23 | 14.23 | 11.33 | 11.23 | 10.98 | 10.93 | 10.88 | 10.73 | 10.68 |
| (E) | Macrogol 4000 (PEG 4000) | 5.47 | 15.3 | 0.6 | 13.23 | 14.23 | 11.33 | 11.23 | 10.98 | 10.93 | 10.88 | 10.73 | 10.68 |
| (F) | Glycerin | 2.48 | 2.5 | 2.5 | 2.48 | 2.48 | 2.48 | 2.48 | 2.48 | 2.48 | 2.48 | 2.48 | 2.48 |
| (D) | Water | Balance | Balance | Balance | Balance | Balance | Balance | Balance | Balance | Balance | Balance | Balance | Balance |
| Total (% by weight) | | 100 | 100 | 100 | 100 | 100 | 100 | 100 | 100 | 100 | 100 | 100 | 100 |
| Separation suppression | | 5 | 5 | 4 | 5 | 5 | 5 | 5 | 5 | 5 | 5 | 5 | 5 |
| Coloration suppression | | ◎ | ◎ | ◎ | ◎ | ◎ | ◎ | ◎ | ◎ | ◎ | ◎ | ◎ | ◎ |
| Feeling of use | | ◎ | ◎ | ◎ | ◎ | ◎ | ○ | ◎ | ◎ | ◎ | ○ | Δ | ◎ |

(*) Soft silicic anyhydride

TABLE 6

| | | Examples | | | | | | | | | | |
|---|---|---|---|---|---|---|---|---|---|---|---|---|
| | | 41 | 42 | 43 | 44 | 45 | 46 | 47 | 48 | 49 | 50 | 51 |
| (A) | Zinc chloride | 44.05 | 44.05 | 44.05 | 44.05 | 40 | 20 | 60 | 44.05 | 44.05 | 44.05 | 44.05 |
| (B) | Zinc oxide | | | | | | | | | | | |
| (B) | Silicon dioxide (*) | 6 | 6 | 6 | 6.15 | 6 | 6 | 6 | 4.5 | 4.5 | 3.3 | 6 |
| (B) | Titanium oxide | 6 | 6 | 6 | 6.15 | 6 | 6 | 6 | 3 | 1 | 9 | |
| (B) | Talc | | | | | | | | | | | 6 |
| | Aluminum oxide | | | | | | | | | | | |
| | Bentonite | | | | | | | | | | | |
| (c1) | HPMC(60SH-4000)2910 | 0.1 | 0.2 | 0.492 | 0.492 | | | | 0.492 | 0.492 | 0.492 | 0.492 |
| (c1) | HPMCP | | | | | | | | | | | |
| (c3) | Poloxamer | | | | | | | | | | | |
| (E) | Macrogol 400 (PEG 400) | 10.18 | 10.13 | 9.98 | 9.83 | 12.25 | 22.25 | 2.25 | 12.23 | 13.23 | 9.83 | 9.98 |
| (E) | Macrogol 4000 (PEG 4000) | 10.18 | 10.13 | 9.98 | 9.83 | 12.25 | 22.25 | 2.25 | 12.23 | 13.23 | 9.83 | 9.98 |
| (F) | Glycerin | 2.48 | 2.48 | 2.48 | 2.48 | 2.48 | 2.48 | 2.48 | 2.48 | 2.48 | 2.48 | 2.48 |
| (D) | Water | Balance | Balance | Balance | Balance | Balance | Balance | Balance | Balance | Balance | Balance | Balance |
| Total (% by weight) | | 100 | 100 | 100 | 100 | 100 | 100 | 100 | 100 | 100 | 100 | 100 |
| Separation suppression | | 5 | 5 | 5 | 5 | 5 | 5 | 5 | 5 | 5 | 5 | 5 |
| Coloration suppression | | ◎ | ◎ | ◎ | ◎ | ◎ | ◎ | ◎ | ◎ | ◎ | ◎ | ◎ |
| Feeling of use | | ◎ | ○ | Δ | Δ | ◎ | ◎ | ◎ | ○ | ◎ | ○ | ◎ |

(*) Soft silicic anyhydride

TABLE 7

|   |   | Comparative Examples | | | | | | | |
|---|---|---|---|---|---|---|---|---|---|
|   |   | 22 | 23 | 24 | 25 | 26 | 27 | 28 | 29 |
| (A) | Zinc chloride | 30 | 50 | 60 | 49.2 | 29.5 | 49.2 | 30 | 30 |
| (A) | Zinc oxide | | | | | | | | |
| (B) | Silicon dioxide (*) | | | | | | | | |
| (B) | Titanium oxide | | | | | | | | |
| (B) | Talc | | | | | | | | |
|   | Aluminum oxide | 25 | 12.5 | 12.5 | | | | | |
|   | Bentonite | | | | 12.3 | | | | |
| (c1) | HPMC (60SH-4000) 2910 | 0.5 | 0.5 | 0.5 | 0.492 | 0.5 | 0.5 | 1 | 2 |
| (c1) | HPMC | | | | | | | | |
| (c3) | Poloxamer | | | | | | | | |
| (E) | Macrogol 400 (PEG 400) | 15.56 | 14.32 | 4.3 | 5.47 | 22.7 | 11.6 | 32.8 | 32.3 |
| (F) | Macrogol 4000 (PEG 4000) | 15.56 | 14.32 | 4.3 | 5.47 | 22.7 | 11.6 | 32.8 | 32.3 |
| (F) | Glycerin | | | | 2.48 | | 2.5 | | |
| (D) | Water | Balance | Balance | Balance | Balance | Balance | Balance | Balance | Balance |
|   | Total (% by weight) | 100 | 100 | 100 | 100 | 100 | 100 | 100 | 100 |
|   | Separation suppression | — | — | — | — | — | — | 5 | 5 |
|   | Coloration suppression | × | × | × | × | × | × | × | × |
|   | Feeling of use | — | ◎ | — | × | — | ◎ | ○ | ○ |

|   |   | Comparative Examples | | | | | | |
|---|---|---|---|---|---|---|---|---|
|   |   | 30 | 31 | 32 | 33 | 34 | 35 | 36 |
| (A) | Zinc chloride | 30 | 49.2 | 30 | 60 | 60 | 50 | 30 |
| (A) | Zinc oxide | | | | | | | |
| (B) | Silicon dioxide (*) | | | | | | | |
| (B) | Titanium oxide | | | | | | | |
| (B) | Talc | | | | | | | |
|   | Aluminum oxide | | | | | | | |
|   | Bentonite | | | | | | | |
| (c1) | HPMC (60SH-4000) 2910 | 2 | 2 | | | | | |
| (c1) | HPMC | | | 5 | 5 | 10 | | |
| (c3) | Poloxamer | | | | | | 26.64 | |
| (E) | Macrogol 400 (PEG 400) | 29.8 | 10.9 | 28.31 | 13.3 | 5.8 | | 23.32 |
| (F) | Macrogol 4000 (PEG 4000) | 29.8 | 10.9 | 28.31 | 13.3 | 5.8 | | 23.32 |
| (F) | Glycerin | | 2.5 | | | | | |
| (D) | Water | Balance | Balance | Balance | Balance | Balance | Balance | Balance |
|   | Total (% by weight) | 100 | 100 | 100 | 100 | 100 | 100 | 100 |
|   | Separation suppression | 5 | — | 5 | 5 | 5 | — | — |
|   | Coloration suppression | × | × | × | × | × | × | × |
|   | Feeling of use | ○ | △ | ◎ | — | — | — | — |

(*) Soft silicic anyhydride

TABLE 8

|   |   | Examples | | | | |
|---|---|---|---|---|---|---|
|   |   | 52 | 53 | 54 | 55 | 56 |
| (A) | Zinc chloride | 50 | 50 | 44.05 | 44.05 | 44.05 |
| (A) | Zinc oxide | | | | | |
| (B) | Silicon dioxide (*) | | | | 2 | 2 |
| (B) | Titanium oxide | 12.5 | 12.5 | 12.3 | 6 | 6 |
| (B) | Talc | | | | | |
|   | Aluminum oxide | | | | | |
|   | Bentonite | | | | | |
| (c1) | HPMC (60SH-4000) 2910 | 1 | 0.5 | 0.492 | | 0.2 |
| (c1) | HPMCP | | | | | |
| (c3) | Poloxamer | | | | | |
| (E) | Macrogol 400 (PEG 400) | 5.8 | 5.56 | 9.83 | 12.23 | 12.13 |
| (E) | Macrogol 4000 (PEG 4000) | 5.8 | 5.56 | 9.83 | 12.23 | 12.13 |
| (F) | Glycerin | 2.52 | 2.52 | 2.48 | 2.48 | 2.48 |
| (D) | Water | Balance | Balance | Balance | Balance | Balance |
|   | Total (% by weight) | 100 | 100 | 100 | 100 | 100 |
|   | Separation suppression | 5 | 5 | 5 | 5 | 4 |
|   | Coloration suppression | ○ | ○ | ⊙ | ⊙ | ⊙ |

TABLE 9

| | | Example 33 | Example 35 | Example 38 | Example 41 | Example 51 |
|---|---|---|---|---|---|---|
| (A) | Zinc chloride | 44.05 | 44.05 | 44.05 | 44.05 | 44.05 |
| (B) | Zinc oxide | | | | | |
| (B) | Silicon dioxide (Soft silicic anhydride) | 4 | 4 | 4.5 | 6 | 6 |
| (B) | Titanium oxide | | 6 | 6 | 6 | |
| (B) | Talc | | | | | 6 |
| | Aluminum oxide | | | | | |
| | Bentonite | | | | | |
| (c1) | HPMC (60SH-4000) 2910 | | | 0.2 | 0.1 | 0.492 |
| (c1) | HPMCP | | | | | |
| (c3) | Poloxamer | | | | | |
| (E) | Macrogol 400 (PEG 400) | 14.23 | 11.23 | 10.88 | 10.18 | 9.98 |
| (E) | Macrogol 4000 (PEG 4000) | 14.23 | 11.23 | 10.88 | 10.18 | 9.98 |
| (F) | Glycerin | 2.48 | 2.48 | 2.48 | 2.48 | 2.48 |
| (D) | Water | Balance | Balance | Balance | Balance | Balance |
| Total (% by weight) | | 100 | 100 | 100 | 100 | 100 |
| Feeling of use | | ⊙ | ⊙ | ○ | ⊙ | ⊙ |
| (i) Presence or absence of fluidity and presence or absence of fear of dripping from application site | | Has no fluidity and low possibility of dripping | Has no fluidity and low possibility of dripping | Has no fluidity and low possibility of dripping | Has no fluidity and low possibility of dripping | Has no fluidity and low possibility of dripping |
| (ii) Ease of spreading on vulnerable affected areas | | Has moderate spreadability and easy to spread on affected areas | Has moderate spreadability and easy to spread on affected areas | Has low spreadability and requires force when spreading on affected areas | Has moderate spreadability and easy to spread on affected areas | Has moderate spreadability and easy to spread on affected areas |
| (iii) Ease of handling based on spinnability | | Has no spinnability and easy to handle | Has no spinnability and easy to handle | Has strong spinnability and requires to devise handling | Has no spinnability and easy to handle | Has no spinnability and easy to handle |
| (iv) Ease of viewing applied site | | The topical composition is translucent, and the applied site is hard to be discriminated | The applied site can be easily discriminated | The applied site can be easily discriminated | The applied site can be easily discriminated | The topical composition is translucent, and the applied site is hard to be discriminated |
| (v) Ease of uniform mixing during preparation | | Easily uniformly mixed and has uniform appearance | Requires further thorough mixing due to visible particles | Easily uniformly mixed and has uniform appearance | Easily uniformly mixed and has uniform appearance | Requires further thorough mixing due to visible particles |
| Overall evaluation | | Excellent in various characteristics except for visibility | Excellent in various characteristics except for ease of uniform mixing during preparation | Excellent in various characteristics except for ease of spreading and ease of handling | Excellent in all characteristics | Excellent in various characteristics except for visibility, and taking time to take out from tube due to slightly high viscosity |

As shown in the above table, the topical compositions of Comparative Examples 22 to 36 could not achieve both separation suppression and coloration suppression, whereas the topical compositions of Examples 29 to 56 could achieve both separation suppression and coloration suppression.

Moreover, among the topical compositions of Examples 29 to 56, the topical compositions of Examples 34 to 50 and 52 to 56 containing titanium oxide in the component (B) had excellent opacity as compared with the topical compositions of 29 to 33 and 51 not containing titanium oxide in the component (B). Further, since the topical compositions of Examples 34 to 50 and 52 to 56 containing titanium oxide in the component (B) had a content of titanium oxide of 10% by weight or less, they were also excellent in that the fluidity of the topical composition was suppressed as compared with cases where the content of titanium oxide exceeded 10% by weight.

Furthermore, among the topical compositions of Examples 34 to 50 and 52 to 56, the topical compositions of Examples 34 to 50 having a content of titanium oxide of 10% by weight or less and a ratio of titanium oxide per 1 part by weight of silicon dioxide of 2.8 parts by weight or less were excellent in that the fluidity was suppressed. That is, the topical compositions of Examples 34 to 50 having high opacity and suppressed fluidity were excellent in that it was very easy to confirm the applied portion, it was very easy to apply the topical composition only to the target place so as not to accidentally apply the highly irritating topical composition to other places, and also it could suppress the applied topical composition from flowing to a place other than the target place.

Further, since the topical compositions of Examples 32 to 51, 55 and 56 containing silicon dioxide in the component (B) had a content of silicon dioxide of 10% by weight or less, they were also excellent in that the properties of the topical compositions were not solidified and were smooth as compared with cases where the content of silicon dioxide exceeded 10% by weight. Then, among the topical compositions of Examples 32 to 51, 55 and 56 containing silicon dioxide in the component (B), the topical compositions of Examples 32 to 51 having a content of silicon dioxide of 3% by weight or more were excellent in that the fluidity was suppressed. Furthermore, among the topical compositions of Examples 34 to 50 containing silicon dioxide and titanium oxide in the component (B), in the topical compositions of Examples 36 to 49 having a content of silicon dioxide of 4.5% by weight or more, uniform mixing during preparation of the topical composition was easier, and particles of the inorganic powder were not visible, resulting in good appearance.

In addition, among the topical compositions of Examples 29 to 33 and 52 to 54 containing a single component as the component (B), the topical compositions of Examples 29 to 33 containing zinc oxide or silicon dioxide as the component (B) were excellent in that the fluidity was suppressed while silicon dioxide and zinc oxide were each singly used. Further, among the topical compositions of Examples 29 to 33, the topical compositions of Examples 32 and 33 containing silicon dioxide as the component (B) were excellent in that the fluidity was suppressed even if the component (C) was not contained.

On the other hand, in the topical compositions of Examples 34, 38 to 44, 48 and 50 containing the component (c1) and containing 3 parts by weight or more of titanium oxide in the component (B), the topical compositions of Examples 37, 40, and 41 having a content of the component (c1) of 0.1% by weight or less were excellent in that usability was improved.

Further, since the topical composition of Example 55 containing talc in the component (B) had a content of talc of 15% by weight or less, it was excellent in that dispersibility of the inorganic powder was good, as compared with cases where the content of talc exceeded 15% by weight. On the other hand, from comparison between the topical composition of Example 51 containing talc in the component (B) and the topical compositions of Examples 29 to 50 containing silicon dioxide, titanium oxide and/or zinc oxide in the component (B), the topical compositions of Examples 29 to 50 containing silicon dioxide, titanium oxide and/or zinc oxide in the component (B) had a moderately low viscosity, so that the topical composition was easily taken out when contained in a tube.

Test Example 3

A topical composition having composition shown in Table 10 was prepared. The preparation was carried out in the same manner as in Test Example 1. The obtained topical composition was evaluated for syneresis suppression and coloration suppression in the same manner as in Test Example 1. The results are shown in Table 10.

TABLE 10

|     |     | Example 57 |
| --- | --- | --- |
| (A) | Zinc chloride | 49 |
| (B) | Zinc oxide | 12.3 |
| (c1) | HPMC (60SH-4000) 2910 | 0.49 |
|     | Starch | — |
| (E) | Macrogol 400 (PEG 400) | 5.47 |
| (E) | Macrogol 4000 (PEG 4000) | 5.47 |
| (F) | Glycerin | 2.5 |
| (D) | Water | Balance |
|     | Total (% by weight) | 100 |
|     | Separation suppression | 5 |
|     | Coloration suppression | ⊙ |

Further, the topical composition of Example 57 was stored at 5° C. for 6 months (condition 1) or at 25° C. for 6 months (condition 2), and thereafter, the feeling of use was evaluated in the same manner as in Test Example 1, based on the starch formulation (49% by weight zinc chloride, 12.3% by weight zinc oxide, 12.3% by weight starch, 2% by weight glycerin, and the balance is water) stored at room temperature for 7 days after preparation. As a result, the evaluation of the topical composition of Example 57 was 0 in both cases of the condition 1 and the condition 2. In the topical composition of Example 61, the viscosity measured by the second method of "2.53 Viscosity Measurement Method" of the 17th revised Japanese Pharmacopoeia was 11.6 kPa·s in the case of the condition 1 and was 6.26 kPa·s in the case of the condition 2, and reduction of viscosity was observed in the case of condition 2, but the reduction of viscosity was not a problem for clinical use. That is, the topical composition of Example 57 is excellent in syneresis suppression and coloration suppression and also has excellent feeling of use even when stored at room temperature for a long period of time, and thus it is considered that it can be effectively used as a commercial preparation.

The invention claimed is:

1. A topical composition comprising:
   (A) 30% to 60% by weight of zinc chloride;
   (B) inorganic powder;
   (C) additive; and
   (D) solvent,
   wherein the component (B) comprises silicon dioxide, and
   wherein the component (C) is selected from the group consisting of:
   (c1) a cellulous derivative in which a hydroxyl group of cellulose is substituted with a substituent selected from the group consisting of —$OR^1$ group, —$OR^2OH$ group, —$OR^3OR^4$ group, and —$OCOR^5$ group, wherein $R^1$ represents an alkyl group having 1 to 3 carbon atoms, $R^2$ represents an alkylene group having 2 to 3 carbon atoms, $R^3$ represents an alkylene group having 1 to 3 carbon atoms, $R^4$ represents an alkyl group having 1 to 3 carbon atoms, and $R^5$ represents an organic group,
   (c2) a polyvinyl-type alcohol selected from the group consisting of polyvinyl alcohol and a derivative thereof, and
   (c3) polyoxyethylene polyoxypropylene glycol, and
   wherein a weight ratio of the component (B) is 9 parts by weight to 60 parts by weight based on 100 parts by weight of the component (A), and
   a weight ratio of the component (C) is 0.1 parts by weight to 13 parts by weight based on 100 parts by weight of the component (A).

2. A topical composition comprising:
   (A) 30% to 60% by weight of zinc chloride;
   (B) inorganic powder;
   (C) additive;
   (D) solvent; and
   (E) polyethylene glycol,
   wherein the component (B) comprises silicon dioxide, and the content of the component (E) is 20% to 45% by weight; and
   wherein the component (C) is selected from the group consisting of
   (c1) a cellulous derivative in which a hydroxyl group of cellulose is substituted with a substituent selected from the group consisting of —$OR^1$ group, —$OR^2OH$ group, —$OR^3OR^4$ group, and —$OCOR^5$ group, wherein $R^1$ represents an alkyl group having 1 to 3 carbon atoms, $R^2$ represents an alkylene group having 2 to 3 carbon atoms, $R^3$ represents an alkylene group having 1 to 3 carbon atoms, $R^4$ represents an alkyl group having 1 to 3 carbon atoms, and $R^5$ represents an organic group,
- (c2) a polyvinyl-type alcohol selected from the group consisting of polyvinyl alcohol and a derivative thereof, and
- (c3) polyoxyethylene polyoxypropylene glycol; and
- wherein a weight ratio of the component (C) is 0.1 parts by weight to 13 parts by weight based on 100 parts by weight of the component (A).

3. The topical composition according to claim 1, wherein the component (c1) is selected from the group consisting of methylcellulose, ethylcellulose, hypromellose, hydroxyethylcellulose, hydroxypropylcellulose, methyl hydroxyethyl cellulose, and an esterified product thereof.

4. The topical composition according to claim 1, wherein the component (D) is water.

5. The topical composition according to claim 1, further comprising (E) polyethylene glycol.

6. The topical composition according to claim 1, further comprising polyoxyethylene polyoxypropylene glycol when the component (C) is the component (c1).

7. The topical composition according to claim 1, wherein an average value of a viscosity grade of the component (c1) is 50 mPa·s or more.

8. The topical composition according to claim 6, wherein an average value of a viscosity grade of the component (c1) is less than 50 mPa·s.

9. The topical composition according to claim 1, further comprising (F) polyhydric alcohol.

10. The topical composition according to claim 9, wherein the component (F) is glycerin.

11. The topical composition according to claim 2, wherein the component (B) further comprises titanium oxide.

12. The topical composition according to claim 1, which is a commercially available preparation.

13. A method for suppressing separation and coloration in a topical composition containing (A) 30% to 60% by weight of zinc chloride and (D) solvent, comprising, in the topical composition, blending (B) inorganic powder and (C) additive together with the component (A) and the component (D), wherein the component (C) is (c1) a cellulous derivative in which a hydroxyl group of cellulose is substituted with a substituent selected from the group consisting of —$OR^1$ group, —$OR^2OH$ group, —$OR^3OR^4$ group, and —$OCOR^5$ group wherein $R^1$ represents an alkyl group having 1 to 3 carbon atoms, $R^2$ represents an alkylene group having 2 to 3 carbon atoms, $R^3$ represents an alkylene group having 1 to 3 carbon atoms, $R^4$ represents an alkyl group having 1 to 3 carbon atoms, and $R^5$ represents an organic group; (c2) a polyvinyl-type alcohol selected from the group consisting of polyvinyl alcohol and a derivative thereof; or (c3) polyoxyethylene polyoxypropylene glycol, wherein the component (B) is selected from the group consisting of silicon dioxide, aluminum silicate, magnesium silicate, magnesium aluminum silicate, sodium magnesium silicate, calcium silicate, talc, calamine, zinc oxide, titanium oxide, iron oxide, aluminum hydroxide, calcium phosphate, and magnesium phosphate, and wherein a weight ratio of the component (B) is 9 parts by weight to 60 parts by weight based on 100 parts by weight of the component (A), and a weight ratio of the component (C) is 0.1 parts by weight to 13 parts by weight based on 100 parts by weight of the component (A).

14. The topical composition according to claim 2, not comprising a cellulose derivative.

15. The topical composition according to claim 2, wherein a weight ratio of the component (B) is 9 parts by weight to 60 parts by weight based on 100 parts by weight of the component (A).

16. The topical composition according to claim 5, wherein the content of the component (E) is 20% to 45% by weight.

* * * * *